(12) United States Patent
Liang

(10) Patent No.: US 7,268,116 B2
(45) Date of Patent: Sep. 11, 2007

(54) METHODS AND COMPOSITIONS FOR PRODUCING SECRETED TRIMERIC RECEPTOR ANALOGS AND BIOLOGICALLY ACTIVE FUSION PROTEINS

(75) Inventor: Peng Liang, Nashville, TN (US)

(73) Assignee: GenHunter Corp., Nashville, TN (US)

( * ) Notice: Subject to any disclaimer, the term of this patent is extended or adjusted under 35 U.S.C. 154(b) by 446 days.

(21) Appl. No.: 10/677,877

(22) Filed: Oct. 2, 2003

(65) Prior Publication Data
US 2005/0202537 A1      Sep. 15, 2005

(51) Int. Cl.
*A61K 38/00*      (2006.01)

(52) U.S. Cl. ..................................................... 514/12

(58) Field of Classification Search ............... 514/12
See application file for complete search history.

(56) References Cited

U.S. PATENT DOCUMENTS

2003/0143564 A1*   7/2003   Burgeson et al. .............. 435/6

FOREIGN PATENT DOCUMENTS

| WO | WO97/17988 | * | 5/1997 |
| WO | WO98/27202 | * | 6/1998 |

OTHER PUBLICATIONS

Mohler et al., Soluble Tumor Necrosis Factor (TNF) Receptors Are Effective Therapeutic Aents in Lethal Endotoxemia and Function Simultaneously as Both TNF Carriers and TNF Antagonists, J. of Immunology, vol. 151, No. 3, p. 1548-1561, 1993.*
Yang et al."Characterization of Stable, Soluble Trimers Containing Complete Ectodomains of Human Immunodeficiency Virus TypeI Envelope Glycoproteins"J.Virol.74:5716-5725(2000).
Frank, S. et al., "Stabilization of Short Collagen-like Triple Helices by Protein Engineering," J. Mol. Biol. 308:1081-1089 (2001).
Chen, B. et al., "A Chimeric Protein of Simian Immunodeficiency Virus Envelope Glycoprotein gp140 and *Escherichia coli* Aspartate Transcarbamoylase"J Virol.78:4508-4516 (2004).

* cited by examiner

Primary Examiner—Karen Cochrane Carlson
Assistant Examiner—Agnes B. Rooke
(74) Attorney, Agent, or Firm—Lambert & Associates; Gary E. Lambert; Adam J. Bruno

(57) ABSTRACT

Methods and compositions for producing secreted soluble receptors and biologically active polypeptides in trimeric forms are disclosed. The process involves fusing the DNA template encoding a soluble receptor with a ligand binding domain or biologically active polypeptide to a DNA sequence encoding a C-propeptide of collagen, which is capable of self-assembly into a covalently linked trimer. The resulting fusion proteins are secreted as trimeric soluble receptor analogs, which can be used for more efficient neutralization of the biological activities of their naturally occurring trimeric ligands.

Figure 2A:
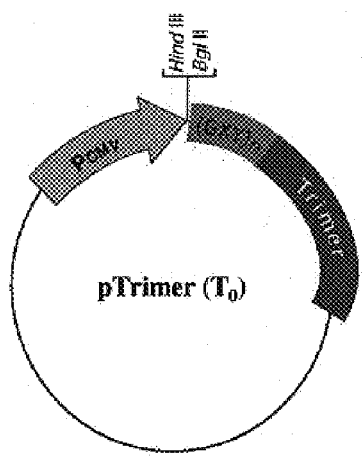

20 Claims, 5 Drawing Sheets
(3 of 5 Drawing Sheet(s) Filed in Color)

Side-View
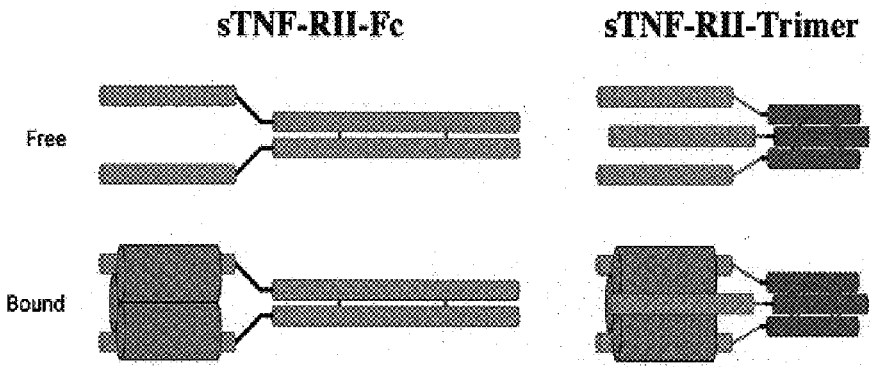
FIG. 1A                  FIG. 1C
Top-View
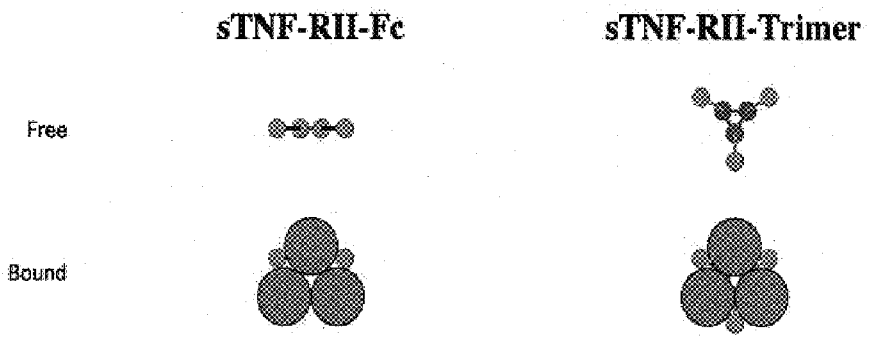
FIG. 1B                  FIG. 1D

METHODS AND COMPOSITIONS FOR PRODUCING SECRETED TRIMERIC RECEPTOR ANALOGS AND BIOLOGICALLY ACTIVE FUSION PROTEINS

FIELD OF THE INVENTION

The present invention relates to methods for protein expression, and more specifically, for creating and expressing secreted and biologically active trimeric proteins, such as trimeric soluble receptors.

BACKGROUND OF INVENTION

In multicellular organisms, such as humans, cells communicate with each other by the so-called signal transduction pathway, in which a secreted ligand (e.g. cytokines, growth factors or hormones) binds to its cell surface receptor(s), leading to receptor activation. The receptors are membrane proteins, which consist of an extracellular domain responsible for ligand binding, a central transmembrane region followed by a cytoplasmic domain responsible for sending the signal downstream. Signal transduction can take place in the following three ways: paracrine (communication between neighboring cells), autocrine (cell communication to itself) and endocrine (communication between distant cells through circulation), depending on the source of a secreted signal and the location of target cell expressing a receptor(s). One of the general mechanisms underlying receptor activation, which sets off a cascade of events beneath the cell membrane including the activation of gene expression, is that a polypeptide ligand such as a cytokine, is present in an oligomeric form, such as a homo-dimer or trimer, which when bound to its monomeric receptor at the cell outer surface, leads to the oligomerization of the receptor. Signal transduction pathways play a key role in normal cell development and differentiation, as well as in response to external insults such as bacterial and viral infections. Abnormalities in such signal transduction pathways, in the form of either underactivation (e.g. lack of ligand) or overactivation (e.g. too much ligand), are the underlying causes for pathological conditions and diseases such as arthritis, cancer, AIDS, and diabetes.

One of the current strategies for treating these debilitating diseases involves the use of receptor decoys, such as soluble receptors consisting of only the extracellular ligand-binding domain, to intercept a ligand and thus overcome the overactivation of a receptor. The best example of this strategy is the creation of Enbrel®, a dimeric soluble TNF-α receptor-immunoglobulin (IgG) fusion protein by Immunex (Mohler et al., 1993; Jacobs et al., 1997), which is now part of Amgen. The TNF family of cytokines is one of the major pro-inflammatory signals produced by the body in response to infection or tissue injury. However, abnormal production of these cytokines, for example, in the absence of infection or tissue injury, has been shown to be one of the underlying causes for diseases such as arthritis and psoriasis. Naturally, a TNF-α receptor is present in monomeric form on the cell surface before binding to its ligand, TNF-α, which exists, in contrast, as a homotrimer (Locksley et al., 2001). Accordingly, fusing a soluble TNF-α receptor with the Fc region of immunoglobulin G1, which is capable of spontaneous dimerization via disulfide bonds (Sledziewski et al., 1992 and 1998), allowed the secretion of a dimeric soluble TNF-α receptor (Mohler et al., 1993; Jacobs et al., 1997). In comparison with the monomeric soluble receptor, the dimeric TNF-α receptor II-Fc fusion has a greatly increased affinity to the homo-trimeric ligand. This provides a molecular basis for its clinical use in treating rheumatoid arthritis (PA), an autoimmune disease in which constitutively elevated TNF-α, a major pro-inflammatory cytokine, plays an important causal role. Although Enbrel® was shown to have a Ki in the pM range (ng/mL) to TNFα (Mohler et al., 1993), 25 mg twice a week subcutaneous injections, which translates to μg/mL level of the soluble receptor, are required for the RA patients to achieve clinical benefits (www.enbrel.com) The high level of recurrent Enbrel® consumption per RA patients has created a great pressure as well as high cost for the drug supply, which limits the accessibility of the drug to millions of potential patients in this country alone.

In addition to the TNF-α family of potent proinflammatory cytokines, the HIV virus that causes AIDS also uses a homo-trimeric coat protein, gp120, to gain entry into CD-4 positive T helper cells in our body (Kwong et al., 1998). One of the earliest events during HIV infection involves the binding of gp120 to its receptor CD-4, uniquely expressed on the cell surface of T helper cells (Clapham et al., 2001). Monomeric soluble CD-4 was shown over a decade ago as a potent agent against HIV infection (Clapham et al., 1989) however, the excitement was sadly dashed when its potency was shown to be limited only to laboratory HIV isolates (Daar et al., 1990). It turned out that HIV strains from AIDS patients, unlike the laboratory isolates, had a much lower affinity to the monomeric soluble CD-4, likely due to the sequence variation on the gp120 (Daar et al., 1990). Although the dimeric soluble CD-4-Fc fusion proteins have been made, these decoy CD-4 HIV receptors showed little antiviral effect against natural occurring HIVs from AIDS patients, both in the laboratories and in clinics, due to the low affinity to the gp120 (Daar et al., 1990).

Clearly, there is a great need to be able to create secreted homo-trimeric soluble receptors or biologically active proteins, which can have perfectly docked binding sites, hence higher affinity, to their naturally occurring homo-trimeric ligands, such as the TNF family of cytokines and HIV coat proteins. Such trimeric receptor decoys theoretically should have a much higher affinity than its dimeric counterparts to their trimeric ligand. Such rationally designed soluble trimeric receptor analogs could significantly increase the clinical benefits as well as lower the amount or frequency of the drug injections for each patient. To be therapeutically feasible, like immunoglobulin Fc, the desired trimerizing protein moiety should ideally be part of a naturally secreted protein that is both abundant in the body and capable of efficient self-trimerization.

Collagen is a family of fibrous proteins that are the major components of the extracellular matrix. It is the most abundant protein in mammals, constituting nearly 25% of the total protein in the body. Collagen plays a major structural role in the formation of bone, tendon, skin, cornea, cartilage, blood vessels, and teeth (Stryer, 1988). The fibrillar types of collagen I, II, III, IV, V, and XI are all synthesized as larger trimeric precursors, called procollagens, in which the central uninterrupted triple-helical domain consisting of hundreds of "GX-Y" repeats (or glycine repeats) is flanked by non-collagenous domains (NC), the N-propeptide and the C-propeptide (Stryer, 1988). Both the C- and N-terminal extensions are processed proteolytically upon secretion of the procollagen, an event that triggers the assembly of the mature protein into collagen fibrils which forms an insoluble cell matrix (Prockop et al., 1998). The shed trimeric C-propeptide of type I collagen is found in the blood of normal people at a concentration in the range of 100-600 ng/mL, with children having a higher level which is indicative with active bone formation.

Type I, IV, V and XI collagens are mainly assembled into heterotrimeric forms consisting of either two α-1chains and one α-2 chain (for Type I, IV, V), or three different α chains (for Type XI), which are highly homologous in sequence. The type II and III collagens are both homotrimers of α-1chain. For type I collagen, the most abundant form of collagen, stable α-1(I) homotrimer is also formed and is present at variable levels (Alvares et al., 1999) in different tissues. Most of these collagen C-propeptide chains can self-assemble into homotrimers, when over-expressed alone in a cell. Although the N-propeptide domains are synthesized first, molecular assembly into trimeric collagen begins with the in-register association of the C-propeptides. It is believed the C-propeptide complex is stabilized by the formation of interchain disulfide bonds, but the necessity of disulfide bond formation for proper chain registration is not clear. The triple helix of the glycine repeats and is then propagated from the associated C-termini to the N-termini in a zipper-like manner. This knowledge has led to the creation of non-natural types of collagen matrix by swapping the C-propetides of different collagen chains using recombinant DNA technology (Bulleid et al., 2001). Non-collagenous proteins, such as cytokines and growth factors, also have been fused to the N-termini of either pro-collagens or mature collagens to allow new collagen matrix formation, which is intended to allow slow release of the noncollagenous proteins from the cell matrix (Tomita et al., 2001). However, under both circumstances, the C-propeptides are required to be cleaved before recombinant collagen fibril assembly into an insoluble cell matrix.

SUMMARY OF THE INVENTION

Disclosed here is an invention that allows any soluble receptors or biologically active polypeptides to be made into trimeric forms as secreted proteins. The essence of the invention is to fuse any soluble receptors and biologically active proteins in-frame to the C-propeptide domain of fibrillar collagen, which is capable of self-trimerization, using recombinant DNA technology. The resulting fusion proteins when expressed in eukaryotic cells are secreted as soluble proteins essentially all in trimeric forms covalently strengthened by inter-molecular disulfide bonds formed among three C-propeptides.

In one aspect of the invention, a method for producing secreted trimeric fusion proteins is disclosed, comprising the following: (a) introducing into a eukaryotic host cell a DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization; (b) growing the host cell in an appropriate growth medium under physiological conditions to allow the secretion of a trimerized fusion protein encoded by said DNA sequence; and (c) isolating the secreted trimeric fusion protein from a host cell.

Within one embodiment, the signal peptide sequence is the native sequence of the protein to be trimerized. Within another embodiment, the signal peptide sequence originates from a secreted protein different from that to be trimerized. Within one embodiment, the non-collagen polypeptide to be trimerized is a soluble receptor consisting of the ligand binding domain(s). Within one embodiment, the C-terminal portion of collagen is the C-propeptide without any triple helical region of collagen SEQ ID NOs:3-4). Within another embodiment, the C-terminal collagen consists of a portion of the triple helical region of collagen as linker to the non-collagenous proteins to be trimerized (SEQ ID NOs:1-2). Within another embodiment, the C-terminal portion of collagen has a mutated or deleted BMP-1 protease recognition site (SEQ ID NOs:3-4).

In one aspect of the invention, a method for producing a secreted trimeric fusion protein is disclosed, comprising the following: (a) introducing into a eukaryotic host cell a DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization, selected from pro.alpha.1(I), pro.alpha.2(I), pro.alpha.1(II), pro.alpha.1(III), pro.alpha.1(V), pro.alpha.2(V), pro.alpha.1(XI), pro.alpha.2(XI) and pro.alpha.3(XI); (b) growing the host cell in an appropriate growth medium under physiological conditions to allow the secretion of a trimerized fusion protein encoded by said DNA sequence; and (c) isolating the secreted trimeric fusion protein from a host cell.

In a preferred embodiment, the non-collagen polypeptide to be trimerized is the soluble TNF-RII (p75) (SEQ ID NOs:9-12). In another preferred embodiment, the non-collagen polypeptide to be trimerized is soluble CD-4, the co-receptor of HIV SEQ ID NOs:13-16). In yet another be trimerized is a placental secreted alkaline phosphatase (SEQ ID NOs:5-8).

In one aspect of the invention, a method for producing a secreted trimeric fusion protein is disclosed, comprising the following: (a) introducing into a eukaryotic host cell a first DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization, selected from pro.alpha.1(I), pro.alpha.2(I), pro.alpha.1(II), pro.alpha.1(III), pro.alpha.1(V), pro.alpha.2(V), pro.alpha.1(XI), pro.alpha.2(XI) and pro.alpha.3(XI); (b) introducing into a eukaryotic host cell a second DNA construct comprising a promoter which drives the transcription of an open reading frame consisting of a second signal peptide sequence which is linked in-frame to a second non-collagen polypeptide to be trimerized, which in turn is joined in-frame to the second C-terminal portion of collagen capable of self-trimerization, selected from pro.alpha.1(I), pro.alpha.2(I), pro.alpha.1(II), pro.alpha.1(III), pro.alpha.1(V), pro.alpha.2(V), pro.alpha.1(XI), pro.alpha.2(XI) and pro.alpha.3(XI); (c) growing the host cell in an appropriate growth medium under physiological conditions to allow the secretion of a trimerized fusion protein encoded by said first and second DNA sequences; and (d) isolating the secreted trimeric fusion protein from the host cell.

In one aspect of the invention, a method for producing a secreted trimeric fusion protein is disclosed, comprising the following: (a) introducing into a eukaryotic host cell a first DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization, selected from pro.alpha.1(I), pro.alpha.2(I), pro.alpha.1(II), pro.alpha.1(III), pro.alpha.1(V), pro.alpha.2(V), pro.alpha.1(XI), pro.alpha.2(XI) and pro.alpha.3(XI); (b) introducing into a eukaryotic host cell a second DNA construct comprising a promoter which drives the transcription of an open reading frame consisting of a second signal peptide sequence which is linked in-frame to a second non-collagen polypeptide to be trimerized, which in turn is joined in-frame to a second C-terminal portion of collagen capable of self-trimerization, selected from pro.alpha.1(I), pro.alpha.2(I), pro.alpha.1(II), pro.alpha.1(III), pro.alpha.1(V), pro.alpha.2(V), pro.alpha.1(XI), pro.alpha.2(XI) and pro.alpha.3(XI); (c) introducing into a eukaryotic host cell a third DNA construct comprising a promoter which drives the transcription of an open reading frame consisting of a third signal peptide sequence which is linked in-frame to a third non-collagen polypeptide to be trimerized, which in turn is joined in-frame to a third C-terminal portion of collagen capable of self-trimerization, selected from pro.alpha.1(I), pro.alpha.2(I), pro.alpha.1(II), pro.alpha.1(III), pro.alpha.1(V), pro.alpha.2(V), pro.alpha.1(XI), pro.alpha.2(XI) and pro.alpha.3(XI); (d) growing the host cell in an appropriate growth medium under physiological conditions to allow the secretion of a trimerized fusion protein encoded by said first and second DNA sequences; and (e) isolating the secreted trimeric fusion protein from the host cell.

The following are the advantages of this invention: (1) collagen is the most abundant protein secreted in the body of a mammal, constituting nearly 25% of the total proteins in the body; (2) the major forms of collagen naturally occur as trimeric helixes, with their globular C-propeptides being responsible for the initiating of trimerization; (3) the trimeric C-propeptide of collagen proteolytically released from the mature collagen is found naturally at sub microgram/mL level in the blood of mammals and is not known to be toxic to the body; (4) the linear triple helical region of collagen can be included as a linker with predicted 2.9 Å spacing per residue, or excluded as part of the fusion protein so the distance between a protein to be trimerized and the C-propeptide of collagen can be precisely adjusted to achieve an optimal biological activity; (5) the recognition site of BMP1 which cleaves the C-propeptide off the procollagen can be mutated or deleted to prevent the disruption of a trimeric fusion protein; (6) the C-propeptide domain provides a universal affinity tag, which can be used for purification of any secreted fusion proteins created by this invention.

In contrast to the Fc Tag technology (Sledziewski et al., 1992 and 1998), with which secreted dimeric fusion proteins can be created, this timely invention disclosed herein enables the creation and secretion of soluble trimeric fusion proteins for the first time. Given the fact that a homotrimer has 3fold symmetry, whereas a homodimer has only 2-fold symmetry, the two distinct structural forms theoretically can never be perfectly overlaid (FIGS. 1A-1D). As such, neither the homodimeric soluble TNF-R-Fc (e.g. Enbrel®), nor the soluble CD4-Fc fusion proteins, could have had an optimal interface for binding to their corresponding homotrimeric ligands, TNF-α and HIV gp120, respectively. In contrast, homotrimeric soluble TNF receptors and CD4 created by the current invention are trivalent and structurally have the potential to perfectly dock to the corresponding homotrimeric ligands. Thus, these trimeric soluble receptor analogs can be much more effective in neutralizing the biological activities of their trimeric ligands. With this timely invention, more effective yet less expensive drugs, such as trimeric soluble TNF-R and CD4 described in the preferred embodiments, can be readily and rationally designed to combat debilitating diseases such as arthritis and AIDS. Trimeric soluble gp120 can also be created with this invention, which could better mimic the native trimeric gp120 coat protein complex found on HIV viruses, and used as a more effective vaccine compared to non-trimeric gp120 antigens previously used. Also chimeric antibodies in trimeric form can be created with the current invention, which could endow greatly increased avidity of an antibody in neutralizing its antigen.

BRIEF DESCRIPTION OF DRAWINGS AND SEQUENCE LISTINGS

The patent or application file contains at least one drawing executed in color. Copies of this patent or patent application publication with color drawing(s) will be provided by the Office upon request and payment of the necessary fee.

FIG. 1A, FIG. 1B, FIG. 1C and FIG. 1D is a schematic representation of the method according to the invention compared to prior dimeric immunoglobulin Fc fusion. FIG. 1A is a side elevation view and FIG. 1B is a top plan view: Structural characteristics of a homodimeric soluble sTNF RII receptor-Fc fusion, such as Amgen's Enbrel, in either ligand-free or -bound form as indicated. Domains labeled in green denote soluble TNF-RII. Note that the Fc (labeled in light blue with inter-chain disultfie bonds in red) fusion protein is dimeric in structure. Given its 2-fold symmetry, the dimeric Fc fusion protein is bivalent and thus theoretically does not have the optimal conformation to bind to a homotrimeric ligand, such as TNF-α (labeled in brown), which has a 3-fold symmetry. FIG. 1C is a side elevation view and FIG. 1D is a top plan view: Structural characteristics of a trimeric soluble sTNF RII receptor-C-propeptide fusion. Given its 3-fold symmetry, a sTNF RII-Trimer fusion protein is trivalent in nature, thus can perfectly dock to its trimeric ligand TNF-α. C-propeptide of collagen capable of self trimerization is labeled in dark blue with inter-chain disulfide bonds labeled in red.

Figure 2B:
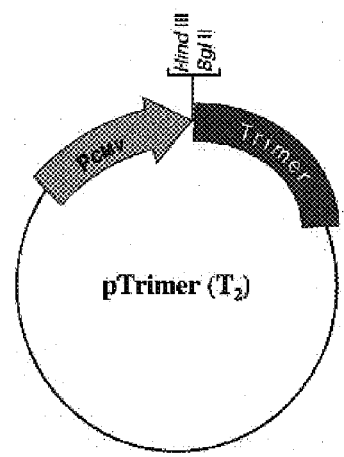
Figure 3A:
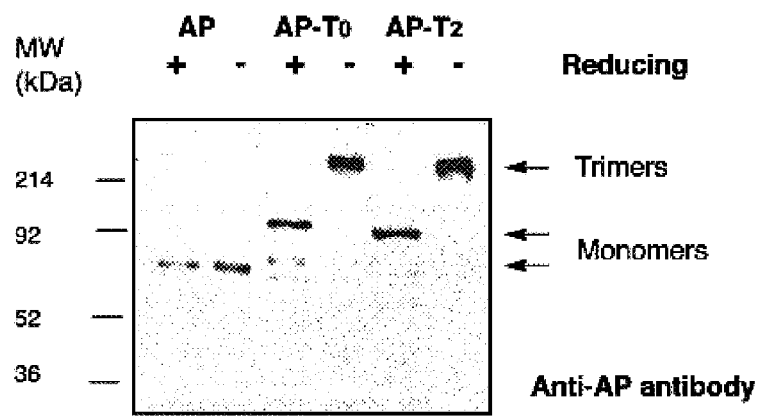
Figure 3B:
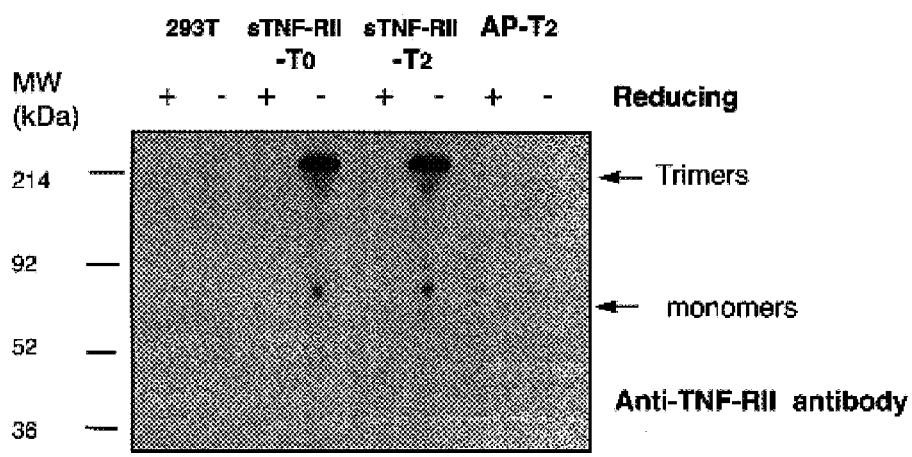

FIG.2A and FIG. 2B illustrate the structures of pTRIMER plasmid vectors for creating secreted trimeric fusion proteins. Any soluble receptor- or biological active polypeptide-encoding cDNAs can be cloned into the unique Hind III or Bgl II sites to allow in-frame fusion at the C-termini to the α (I) collagen containing C-propetide sequence for trimerization. FIG. 2A: The pTRIMER(T0) construct contains part of the glycine-repeats (GXY)n upstream of the C-propeptide; FIG. 2B: whereas the pTRIMER(T2) contains only the C-propeptide domain with a mutated BMP-1 protease recognition site. FIG. 3A and FIG. 3B illustrate the expression and secretion of disulfide bond-linked trimeric collagen fusion proteins.

FIG. 3A. Western blot analysis of the trimerization of human placental alkaline phosphatase (AP) when fused to the C-propeptides of α(I) collagen. The expression vectors encoding either AP alone or AP-C-propeptide fusions in pTRIMER vectors were transiently transfected into HEK293T cells. Forty-eight hours later, the conditioned media (20 μL) of each transfected cells as indicated were boiled for 5 minutes in equal volume of 2X SDS sample buffer either with or without reducing agent (mercaptoethanol), separated on a 10% SDS-PAGE and analyzed by Western blot using a polyclonal antibody to AP (GenHunter Corporation). Note the secreted 67 kDa AP alone does not form intermolecular disulfide bonds, whereas the secreted AP-T0 and AP-T2 fusions both are assembled efficiently into disulfide bond linked timers.

FIG. 3B. Western blot analysis of the trimerization of soluble human TNF-RII when fused to the C-propeptides of α (I) collagen. The expression vectors encoding either the AP-C-propeptide fusion (T2) (as a negative control for antibody specificity), or human soluble TNF-RII-C-propeptide fusions as indicated in pTRIMER vectors were transiently transfected into HEK293T cells. Forty-eight hours later, the conditioned media (20 μL) of each non-transfected and transfected cells as indicated were boiled for 5 minutes in equal volume of 2X SDS sample buffer either with or without reducing agent (mercaptoethanol), separated on a 10% SDS-PAGE and analyzed by Western blot using a monoclonal antibody to human TNF-RII (clone 226, R & D Systems, Inc.). Note the monoclonal antibody can only recognize the secreted TNF-RII with disulfide bonds. Both the soluble TNF-RII-T0 and TNF-RII-T2 fusions are assembled efficiently into disulfide bond linked trimers.

Figure 4:
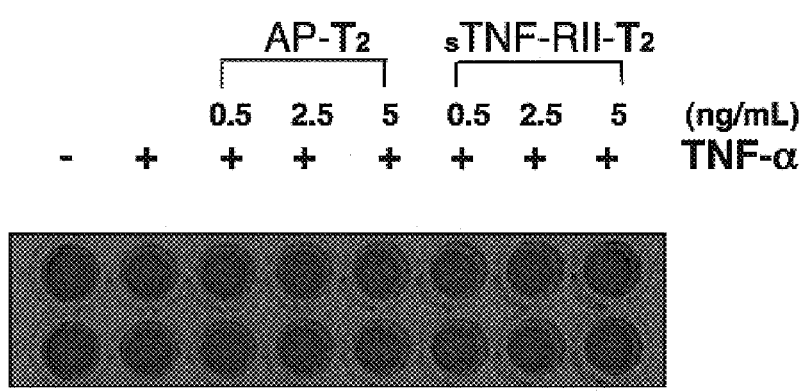
Figure 5:
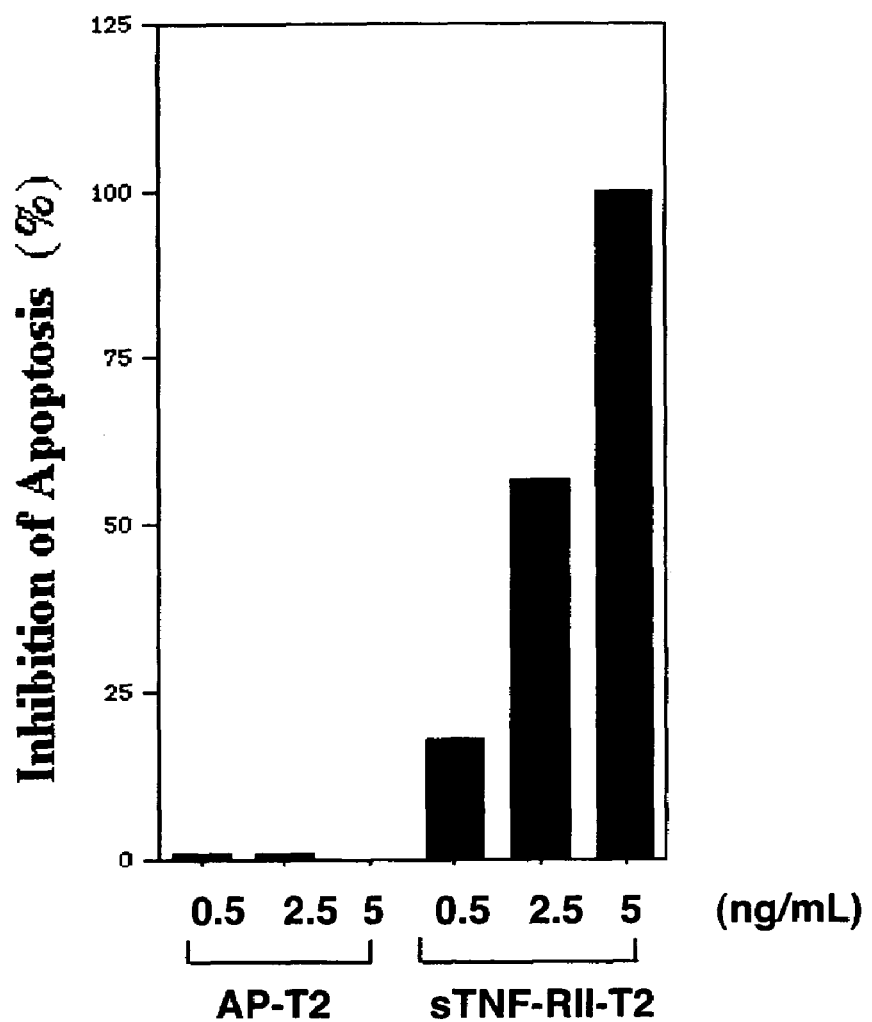

FIG. 4 and FIG. 5. illustrate the bioassays showing the potent neutralizing activity of the trimeric soluble human TNF-RII-C-propeptide fusion protein against human TNF-α mediated apoptosis.

FIG. 4. The TNF-α sensitive WEHI-13VAR cells (ATCC) were resuspended at 1 million cells/mL in RPMI medium containing 10% FBS. 100 μL of the cell suspension was plated into each well in a 96-well microtiter plate. Actinomycin D was added to each well at 500 ng/mL concentration followed by human TNF-α at 500 pg/ml (R & D Systems) in the presence or absence of trimeric soluble human TNF-RII-T2 as indicated. As a negative control, the trimeric AP-T2 was added in place of TNF-RII-T2. After 16 hours of incubation in a tissue culture incubator, the viability of cells was examined using either an inverted microscope at 20X magnification or cell viability indicator dye, Alamar Blue (BioSource, Inc.) added to 10% (v/v) to each well. The live cells are able to turn the dye color from blue to pink. Note that the trimeric soluble human TNF-RII-T2 exhibits a potent neutralizing activity against TNF-α protects the cells from TNF-α mediated apoptosis.

DESCRIPTION OF SEQUENCE LISTINGS

SEQ ID No. 1 (963 bases)

Nucleotide sequence encoding the C-propeptide human collagen α(I) T0 construct. The cDNA construct was cloned into the pAPtag2 vector, replacing the AP coding region. The underlined sequences denote restriction enzyme sites used in constructing the corresponding pTRIMER vector. The bolded codons denote the start and the stop of the T0 coding region.

SEQ ID No. 2 (311 aa)

The predicted C-propeptide T0 protein sequence of human Collagen α(I). The underlined sequence denotes the region of the "glycine repeats" upstream of the C-propeptide. The amino acid residues in red indicate the BMP-1 protease recognition site.

SEQ ID No. 3 (771 bases)

Nucleotide sequence encoding the C-propeptide of human collagen α(I) T2 construct. The cDNA construct was cloned into pAPtag2 vector, replacing the AP coding region. The underlined sequences denote restriction enzyme sites used in constructing the corresponding pTRIMER vector. The bolded codons denote the start and the stop of the T2 coding region.

SEQ ID No. 4 (247 aa)

The predicted C-propeptide T2 protein sequence of human Collagen α(I). The amino acid residue in red indicates the location of mutated BMP-1 protease recognition site.

SEQ ID No. 5 (2487 bases)

Nucleotide sequence encoding the human placental alkaline phosphatase (AP) fused to the T0 C-propeptide of human α(I) collagen (AP-T0). The underlined sequences indicate the restriction sites used for the fusion construct. The restriction site, which marks the fusion site shown in the middle of the sequence, is Bgl II.

SEQ ID No. 6 (819 aa)

The predicted protein sequence of the AP-T0 fusion protein. The amino acid residues in blue indicate fusion sites between human placental alkaline phosphates (AP) and the α(I) collagen T0 polypeptide. The bolded codons denote the start and the stop of the fusion protein. The underlined sequence denotes the region of the "glycine repeats" upstream of the C-propeptide of human α(I) collagen. The amino acid residues in red indicate the BMP-1 protease recognition sequence.

SEQ ID NO:7 (2294 bases)

Nucleotide sequence encoding the human placental alkaline phosphatase (AP) fused to the T2 C-propeptide human oil) collagen (AP-T2). The bolded codons denote the start and the stop of the fusion protein. The underlined sequences indicate the restriction sites used for the fusion construct. The restriction site, which marks the fusion site shown in the middle of the sequence, is Bgl II.

SEQ ID NO:8 (755 aa)

The predicted protein sequence of the AP-T2 Fusion. The amino acid residues in blue indicate fusion sites between human placental alkaline phosphates (AP) and the α(I) collagen T2 polypeptide. The amino acid residue in red indicates the location of the mutated BMP-1 protease recognition site.

SEQ ID No. 9 (1734 bases)

Nucleotide sequence encoding the human soluble TNF-RII fused to the T0 C-propeptide of human α(I) collagen (sTNF-RII-T0). The bolded codons denote the start and the stop of the fusion protein. The underlined sequences indicate the restriction sites used for the fusion construct. The underlined sequence, which marks the fusion site shown in the middle of the sequence, is the BamH I/Bgl II ligated junction.

SEQ ID NO:10 (566 aa)

The predicted protein sequence of the human soluble TNF-RII-T0 Fusion. The amino acid residues in blue indicate fusion sites between human soluble TNF-RII and α (I) collagen T0 polypeptide. The underlined sequence denotes region of the "glycine repeats" upstream of the C-propeptide of human α (I) collagen. The amino acid residues in red indicate the BMP-1 protease recognition site.

SEQ ID NO:11 (1542 bases)

Nucleotide sequence encoding the human soluble TNF-RII fused to the T2 C-propeptide of human α(I) collagen (sTNF-RII-T2). The bolded codons denote the start and the stop of the fusion protein. The underlined sequences indicate the restriction sites used for the fusion construct. The underlined sequence, which marks the fusion site shown in the middle of the sequence, is the BamH/Bgl II ligated junction.

SEQ ID No. 12 (502 aa)

The predicted protein sequence of the human soluble TNF-RII-T2 fusion protein. The amino acid residues in blue indicate fusion sites between human soluble TNF-RII and the α(I) collagen T2 polypeptide. The amino acid residue in red indicates the location of mutated BMP-1 protease recognition site.

SEQ ID No. 13 (2139 bases)

Nucleotide sequence encoding the human soluble CD4 fused to the T0 C-propeptide of human α(I) collagen. The underlined sequences indicate the restriction sites used for the fusion construct. The underlined sequence, which marks the fusion site shown in the middle of the sequence, is the Bgl II site.

SEQ ID No. 14 (699 aa)

The predicted Protein Sequence of the human soluble CD4-T0 Fusion. The amino acid residues in blue indicate fusion sites between human soluble CD4 and α(I) collagen T0 polypeptide. The underlined sequence denotes the region of the "glycine repeats" upstream of the C-propeptide of human α(I) collagen. The amino acid residues in red indicate the BMP-1 protease recognition site.

SEQ ID No. 15 (1947 bases)

Nucleotide sequence encoding the human soluble CD4 fused to the T2 C-propeptide of human α(I) collagen. The underlined sequences indicate the restriction sites used for the fusion construct. The underlined sequence, which marks the fusion site shown in the middle of the sequence, is the Bgl II site.

SEQ ID No. 16 (635 aa)

The predicted Protein Sequence of the human soluble CD4-T2 Fusion. The amino acid residues in blue indicate fusion sites between human soluble CD4 and α(I) collagen T2 polypeptide. The amino acid residue in red indicates the location of mutated BMP-1 protease recognition site.

DESCRIPTION OF THE INVENTION

Prior to setting forth the invention, it may be helpful to an understanding thereof to set forth definitions of certain terms to be used hereinafter.

DNA Construct: A DNA molecule, generally in the form of a plasmid or viral vector, either single- or double-stranded that has been modified through recombinant DNA technology to contain segments of DNA joined in a manner that as a whole would not otherwise exist in nature. DNA constructs contain the information necessary to direct the expression and/or secretion of the encoding protein of interest.

Signal Peptide Sequence: A stretch of amino acid sequence that acts to direct the secretion of a mature polypeptide or protein from a cell. Signal peptides are characterized by a core of hydrophobic amino acids and are typically found at the amino termini of newly synthesized proteins to be secreted or anchored on the cell surface. The signal peptide is often cleaved from the mature protein during secretion. Such signal peptides contain processing sites that allow cleavage of the signal peptides from the mature proteins as it passes through the protein secretory pathway. A signal peptide sequence when linked to the amino terminus of another protein without a signal peptide can direct the secretion of the fused protein. Most of the secreted proteins, such as growth factors, peptide hormones, cytokines and membrane proteins, such as cell surface receptors, contain a signal peptide sequence when synthesized as a nascent protein.

Soluble receptor: The extracellular domain, in part or as a whole, of a cell surface receptor, which is capable of binding its ligand. Generally, it does not contain any internal stretch of hydrophobic amino acid sequence responsible for membrane anchoring.

C-propeptide of collagens: The C-terminal globular, and non-triple-helical domain of collagens, which is capable of self-assembly into trimers. In contrast to the triple helical region of collagens, the C-propeptide does not contain any glycine repeat sequence and is normally proteolytically removed from procollagen precursor upon procollagen secretion before collagen fibril formation.

Glycine repeats: The central linear triple helix forming region of collagen which contains hundreds of (Gly-X-Y)$_n$ repeats in amino acid sequence. These repeats are also rich in proline at X or/and Y positions. Upon the removal of N-and C-propeptides, the glycine-repeats containing collagen triple helices can assemble into higher order of insoluble collagen fibrils, which makes up the main component of the cell matrix.

cDNA: Stands for complementary DNA or DNA sequence complementary to messenger RNA. In general cDNA sequences do not contain any intron (non-protein coding) sequences.

Prior to this invention, nearly all therapeutic antibodies and soluble receptor-Fc fusion proteins, such as Enbrel®, are dimeric in structure (FIGS. 1A-1D). Although these molecules, compared to their monomeric counterparts, have been shown to bind their target antigens or ligands with increased avidity, it is predicted that they are still imperfect, due to structural constrains, to bind their targets that have a homotrimeric structure. Examples of such therapeutically important trimeric ligands include TNF family of cytokines and HIV coat protein gp120. Therefore, from a structural point of view, it will be desirable to be also able to generate trimeric soluble receptors or antibodies, which can perfectly dock to their target trimeric ligands or antigens (FIGS. 1A-1D), and thereby completely block the ligand actions. Such trimeric soluble receptors or chimeric antibodies are expected to have the highest affinity to their targets and thus can be used more effectively and efficiently to treat diseases such as arthritis and AIDS.

This invention discloses ways for generating such secreted trimeric receptors and biological active proteins by fusing them to the C-propeptides of collagen, which are capable of selfassembly into trimers. The following are the advantages of this invention: (1) collagen is the most abundant protein secreted in the body of a mammal, constituting nearly 25% of the total protein in the body; (2) the major forms of collagen naturally occur as trimeric helixes, with their globular C-propeptides responsible for the initiating of trimerization, which are subsequently proteolytically cleaved upon triple helix formation; (3) the cleaved soluble trimeric C-propeptide of collagen is found naturally at sub microgram/mL level in the blood of mammals; (4) the linear triple helical region of collagen can be included as a linker or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptides domain provides a universal affinity tag, which can be used for purification of any secreted fusion proteins created by this invention; (7) unlike the IgG1 Fc tag which is known to be have other biological functions such as binding to its own cell surface receptors, the only known biological function of the C-propeptide of collagen is its ability to initiate trimerization of nascent procollagen chains and keep the newly made procollagen trimer soluble before assembly into insoluble cell matrix. These unique properties of the C-propeptide of collagen would predict that this unique trimerization tag is unlikely going to be toxic, or immunogenic, making it an ideal candidate for therapeutic applications.

To demonstrate the feasibility for making secreted trimeric fusion proteins, cDNA sequences encoding the entire C-propeptides of human α1 (I) containing either some glycine-repeat triple helical region (T0construct, SEQ ID NOs:1-2), or no glycine-repeat with a mutated BMP-1 recognition site (T2 construct, SEQ ID NOs:1-2) were amplified by RT-PCR using EST clones purchased from the American Type Culture Collection (ATCC) The amplified cDNAs were each cloned as a Bgl II-XbaI fragment into the pAPtag2 mammalian expression vector (Genhunter Corporation; Leder et al., 1996 and 1998), replacing the AP coding region (FIG. 2). The resulting vectors are called pTRIMER, versions T2 and T0, respectively. The vectors allow convenient in-frame fusion of any cDNA template encoding a soluble receptor or biologically active protein at the unique Hind III and Bgl II sites. Such fusion proteins have the collagen trimerization tags located at the C termini, similar to native procollagens.

EXAMPLE 1

To demonstrate the feasibility of this invention, a cDNA encoding the human secreted placental alkaline phosphatase (AP), including its native signal peptide sequence, was cut out as a Hind III-Bgl II fragment from the pAPtag4 vector (GenHunter Corporation; Leder et al., 1996 and 1998) and cloned into the corresponding sites of the pTRIMER-T0 and pTRIMER-T2 vectors. The resulting AP-collagen fusion constructs (SEQ ID NOs:5-8) were expressed in HEK293T cells (GenHunter Corporation) after transfection. The successful secretion of the AP-collagen fusion proteins can be readily determined by AP activity assay using the conditioned media of the transfected cells. The AP activity reached about 1 unit/mL (or equivalent to about 1 µg/mL of the fusion protein) 2 days following the transfection. To obtain HEK293T cells stably expressing the fusion proteins, stable clones were selected following co-transfection with a puromycine-resistant vector, pBabe-Puro (GenHunter Corporation). Clones expressing AP activity were expanded and saved for long-term production of the fusion proteins.

To determine if the AP-collagen fusion proteins are assembled into disulfide bond-linked trimers, conditioned media containing either AP alone or AP-T0 and AP-T2 fusions were boiled in SDS sample buffers containing either without (non-reducing) or with β-mercaptoethanol (reducing), separated by an SDS PAGE and analyzed by Western blot using an anti-AP polycloning antibody (GenHunter Corporation). AP alone without fusion exhibited as a 67 kDa band under both non-reducing and reducing conditions, consistent with the lack of any inter-molecular disulfide bonds as expected (FIG. 3A). In contrast, both AP-T0 and AP-T2 fusion proteins secreted were shown to be three times as big (about 300 kDa) under the non-reducing condition as those under the reducing condition (90-100 kDa), indicating that both fusion proteins were assembled completely into homotrimers (FIG. 3A). This result essentially reduces the concept of this invention to practice.

EXAMPLE 2

To provide a proof that new and therapeutically beneficial biological functions can be endowed to a trimeric fusion protein, next a trimeric human soluble TNF-RII (p75) receptor using a corresponding EST clone purchased from the ATCC was constructed. As described in Example 1, the N-terminal region of human TNF-RII, including the entire ligand-binding region, but excluding the transmembrane domain, was cloned in-frame, as a Bam H I fragment, into the Bgl II site of both pTRIMER-T0 and pTRIMER-T2 vectors (SEQ ID NOs:9-12). The resulting fusion constructs were expressed in HEK293T cells following transfection. Stable clones were obtained by puromycine co-selection as described in Example 1. Western blot analysis under both non-reducing and reducing conditions was carried out to determine if the resulting soluble TNF-RII-collagen fusion proteins were indeed expressed, secreted and assembled into trimeric forms. As expected, the monoclonal antibody against human TNF-RII (clone 226 from R & D Systems, Inc.) clearly recognized the trimeric soluble TNF-fusion proteins expressed by both T0 and T2 fusion vectors as 220-240 kDa bands, which are about three times bigger than the corresponding monomeric fusion proteins (FIG. 3B). The TNF-RII antibody failed to detect monomeric fusion proteins under reducing conditions, consistent with the property specified by the antibody manufacturer. As a negative control for antibody specificity, neither the HEK293T cell alone, nor the cells expressing AP-T2 fusion protein expressed any TNF-RII (FIG. 3B).

To determine if the trimeric soluble TNF-RII receptors are potent inhibitors of its trimeric ligand TNF-α, TNF-α bioassay was carried out using a cytokine sensitive cell line WEHI-13VAR (ATCC) essentially as described previously (Mohler et al., 1993). The result shown in FIG. 4 clearly indicated that the trimeric soluble TNF-RII-C-propeptide fusion proteins are extremely potent in neutralizing the TNF-α mediated apoptosis of WEHI-13VAR cells in the presence of Actinomycin D (500 ng/mL) (Sigma). When human TNF-α (R & D Systems) was used at 0.5 ng/mL, the trimeric soluble TNF-RII-T2 (both from serum-free media or in purified form) had an apparent Ki-50 (50% inhibition) of about 2 ng/mL or $8 \times 10^{-12}$ M (assuming the MW of 240 kDa as homotrimer). This affinity to TNF-α is 4 orders of magnitude higher than that of the monomeric TNF-RII and at least 10-100 times higher than that of the dimeric soluble TNF-RII-Fc fusion, such as Enbrel (Mohler et al., 1993).

This crucial example proves that this invention can create trimeric fusion proteins with new biological properties that may have great therapeutic applications. Such soluble trimeric human TNF receptors may prove to be much more effective than the current dimeric soluble TNF receptor (e.g. Enbrel) on the market in treating autoimmune diseases such as RA. The dramatically increased potency of trimeric-TNF receptors could greatly reduce the amount of TNF blockers to be injected weekly for each patient, while improving the treatment and significantly lowering the cost for the patients. The improved potency of trimeric TNF receptors should also alleviate the current bottleneck in dimeric TNF receptor production, which currently can only meet the demands in treating about 100,000 patients in the United States.

EXAMPLE 3

The HIV virus, the cause of AIDS, infects and destructs primarily a special lineage of T lymphocytes in our body. These so called CD4+ T cells express a cell surface protein dubbed CD4, which is the receptor of HIV. HIV recognizes the CD4+ cells with its viral coat protein gp120 that binds to CD4. Notably, the gp120 exists as a giant homotrimeric complex on the viral surface, whereas the CD4 is monomeric on the cell surface. The current model for HIV infection is that of a complete docking of HIV to CD4+ T cells, when all three subunits of gp120 trimers are each bound to CD4 is required for viral RNA entry into the cells. Obviously, one of the straightforward strategies for stopping HIV infection is to use soluble CD4 to blind the virus. Indeed, such approach using both monomeric soluble CD4 and CD4-Fc fusions has been shown quite effective in curbing HIV infections of laboratory isolates (Clapham et al., 1989; Daar et al., 1990). Unfortunately, these soluble CD4 were less effective in stopping the infection of HIV viral strains found in AIDS patients (Daar et al., 1990), possibly due to the amino acid sequence variations of the gp120, which lowers the affinity to monomeric and dimeric soluble CD4s.

To significantly increase the affinity of a soluble CD4 to any gp120 variants on HIV viruses, ideally a soluble CD4 should be in trimeric form so it can perfectly dock to its trimeric ligand, gp120 homotrimers. One of the major challenges for combating AIDS has been the high mutational rate of the viral genome, which leads to drug resistance. Therefore any drugs that directly target viral genes, such as HIV reverse transcriptase (e.g. AZT) and protease, are likely rendered ineffective as a result of viral mutations. In contrast, no matter how much it mutates, a HIV virus has to bind to a cellular CD4 receptor to initiate the infection. Thus, a high affinity soluble CD4 trimer should be immune to viral mutations because viral mutations in gp120 genes will render the virus unable to bind not only to a trimeric soluble CD4, but also CD4 on the cells.

To create such trimeric soluble CD4 HIV receptor analogs, a cDNA encoding the entire human soluble CD4, including its native signal peptide sequence, but excluding the transmembrane and the short cytoplasmic domains, was amplified using an EST clone purchased from the ATOC. The resulting cDNA was then cloned as a Hind III-Bgl II fragment into the corresponding sites of the pTRIMER-T0 and pTRIMER-T2 expression vectors. The resulting soluble CD4-collagen fusion constructs (SEQ ID NOs:13-16) were expressed in HEK293T cells (GenHunter Corporation) after transfection. To obtain HEK293T cells stably expressing the fusion proteins, stable clones were selected following co-transfection with a puromycine-resistant vector, pBabe-Puro (GenHunter Corporation) Clones expressing the fusion proteins were expanded and saved for long-term production of the fusion proteins.

To determine if the soluble human CD4-collagen fusion proteins are assembled into disulfide bond-linked trimers, conditioned media containing soluble CD4-T0 and CD4T2 fusions were boiled in SDS sample buffers containing either without (non-reducing) or with β-mercaptoethanol (reducing), separated by a SDS PAGE and analyzed by Western blot using an monoclonal antibody to human CD4 (R & D Systems). Both soluble CD4-T0and CD4-T2 fusion proteins secreted were shown to be three times as big (about 300 kDa) under the non-reducing condition as those under the reducing condition (90-100 kDa), indicating they were assembled essentially completely into homotrimers (data not shown ). Now these trimeric soluble CD4 can be readily tested for gp120 binding and anti-HIV infection.

What is claimed is:

1. A method for generating a secreted disulfide bond-linked trimeric fusion protein, comprising:
(a) creating a DNA construct comprising a transcriptional promoter linked to a template encoding a fused protein subunit comprising a signal peptide sequence followed by in-frame fusion to a non-collagenous polypeptide comprising a ligand binding domain, which in turn is joined by in-frame fusion to a mammalian polypeptide which is heterologous from the non-collagenous polypeptide and which is capable of self-trimerizing said fused protein subunit to form said disulfide bond-linked trimeric fusion protein containing three ligand binding domains, wherein said trimeric fusion protein has an increased binding affinity to a ligand than a monomeric ligand binding domain (b) introducing said DNA construct into a eukaryotic cell; (c) growing said host cell in an appropriate growth medium under physiological conditions to allow said fused protein subunits to trimerize into the disulfide bond-linked trimeric fusion protein and to further allow the secretion of the trimeric fusion-protein; and (d) isolating said secreted trimeric fusion protein from the culture medium of said host cell.

2. The method of claim 1 wherein the disulfide bond-linked trimeric fusion protein is a homotrimer.

3. The method of claim 1 wherein the mammalian polypeptide comprises the C terminal portion of collagen capable of self-assembly into a trimer.

4. The method of any one of claims 1-3, wherein the signal peptide sequence and the noncollagenous polypeptide are both from the same native secreted protein.

5. The method of any one of claims 1-3, wherein the signal peptide sequence and the noncollagenous polypeptide are selected from two different secreted proteins.

6. The method of claim 1, wherein the host eukaryotic cell is a fungal or insect cell.

7. The method of claim 1, wherein the host eukaryotic cell is a cultured mammalian cell line.

8. The method of claim 3, wherein the C-terminal portion of collagen includes a "glycine-repeat" triple helical region of collagen linked to a C-propeptide.

9. The method of claim 3, wherein the C-terminal portion of collagen is encoded by SEQ ID NO:1.

10. The method of claim 3, wherein the C-terminal portion of collagen comprises only a C-propeptide without any glycine-repeat triple helical region of collagen.

11. The method of any one of claims 8-10, wherein the C-terminal portion of collagen comprises a mutated or deleted BMP-1 protease recognition sequence, thereby conferring the trimeric fusion proteins resistance to BMP-1 protease degradation.

12. The method of claim 10 or 11, wherein the C-terminal portion of collagen is encoded by SEQ ID NO:3.

13. The method of claim 3 wherein the C terminal portion of collagen is selected from the group consisting of pro.alpha.1(I), pro.alpha 2(I), pro.alpha.1(II), pro.alpha.1(III), pro.alpha.1(V), pro.alpha.2(V), pro.alpha.1(XI), pro.alpha.2(XI) and pro.alpha.3(XI).

14. The method of claim 13, wherein the C-terminal portion of collagen has the amino acid sequence shown as SEQ ID NO:2.

15. The method of claim 10 or 11, wherein the C-terminal portion of collagen has the amino acid sequence shown as SEQ ID NO: 4.

16. The method of claim 1, wherein the non-collagenous polypeptide is soluble TNF alpha receptor or functional portion thereof.

17. The method of claim 16 wherein the soluble TNF alpha receptor is soluble human TNF alpha receptor or functional portion thereof.

18. The method of claim 16, wherein the soluble TNF alpha receptor is selected from the group consisting of soluble p55 TNF alpha receptor and soluble p75 TNF alpha receptor.

19. The method of claim 1, wherein the ligand is TNF.

20. The method of claim 1, wherein the non-collagenous polypeptide is soluble CD4 receptor or functional portion thereof.

\* \* \* \* \*

SEQUENCE LISTING

<160> NUMBER OF SEQ ID NOS: 16

<210> SEQ ID NO 1
<211> LENGTH: 963
<212> TYPE: DNA
<213> ORGANISM: Homo sapiens
<220> FEATURE:
<221> NAME/KEY: CDS
<222> LOCATION: (12)...(947)

<400> SEQUENCE: 1

```
aagcttacgt aagatctaac ggtctccctg gccccattgg gcccctggt cctcgcggtc      60 gcactggtga tgctggtcct gttggtcccc ccggccctcc tggacctcct ggtccccctg     120
gtcctcccag cgctggtttc gacttcagct tcctgcccca gccacctcaa gagaaggctc     180
acgatggtgg ccgctactac cgggctgatg atgccaatgt ggttcgtgac cgtgacctcg     240
aggtggacac caccctcaag agcctgagcc agcagatcga gaacatccgg agcccagagg     300
gaagccgcaa gaaccccgcc cgcacctgcc gtgacctcaa gatgtgccac tctgactgga     360
agagtggaga gtactggatt gaccccaacc aaggctgcaa cctggatgcc atcaaagtct     420
tctgcaacat ggagactggt gagacctgcg tgtacccac tcagcccagt gtggcccaga     480
agaactggta catcagcaag aaccccaagg acaagaggca tgtctggttc ggcgagagca     540
tgaccgatgg attccagttc gagtatggcg gccagggctc cgaccctgcc gatgtggcca     600
```

```
tccagctgac cttcctgcgc ctgatgtcca ccgaggcctc ccagaacatc acctaccact    660
gcaagaacag cgtggcctac atggaccagc agactggcaa cctcaagaag gccctgctcc    720
tcaagggctc caacgagatc gagatccgcg ccgagggcaa cagccgcttc acctacagcg    780
tcactgtcga tggctgcacg agtcacaccg agcctgggg caagacagtg attgaataca     840
aaaccaccaa gtcctcccgc ctgcccatca tcgatgtggc ccccttggac gttggtgccc    900
cagaccagga attcggcttc gacgttggcc ctgtctgctt cctgtaaact ccctccatct    960
aga                                                                  963
```

<210> SEQ ID NO 2
<211> LENGTH: 311
<212> TYPE: PRT
<213> ORGANISM: Homo sapiens

<400> SEQUENCE: 2

```
Arg Ser Asn Gly Leu Pro Gly Pro Ile Gly Pro Pro Gly Pro Arg Gly
                5                   10                  15

Arg Thr Gly Asp Ala Gly Pro Val Gly Pro Pro Gly Pro Pro Gly Pro
            20                  25                  30

Pro Gly Pro Gly Pro Pro Ser Ala Gly Phe Asp Phe Ser Phe Leu
        35                  40                  45

Pro Gln Pro Pro Gln Glu Lys Ala His Asp Gly Gly Arg Tyr Tyr Arg
    50                  55                  60

Ala Asp Asp Ala Asn Val Val Arg Asp Arg Asp Leu Glu Val Asp Thr
65                  70                  75                  80

Thr Leu Lys Ser Leu Ser Gln Gln Ile Glu Asn Ile Arg Ser Pro Glu
                85                  90                  95

Gly Ser Arg Lys Asn Pro Ala Arg Thr Cys Arg Asp Leu Lys Met Cys
            100                 105                 110

His Ser Asp Trp Lys Ser Gly Glu Tyr Trp Ile Asp Pro Asn Gln Gly
        115                 120                 125

Cys Asn Leu Asp Ala Ile Lys Val Phe Cys Asn Met Glu Thr Gly Glu
    130                 135                 140

Thr Cys Val Tyr Pro Thr Gln Pro Ser Val Ala Gln Lys Asn Trp Tyr
145                 150                 155                 160

Ile Ser Lys Asn Pro Lys Asp Lys Arg His Val Trp Phe Gly Glu Ser
                165                 170                 175

Met Thr Asp Gly Phe Gln Phe Glu Tyr Gly Gly Gln Gly Ser Asp Pro
            180                 185                 190

Ala Asp Val Ala Ile Gln Leu Thr Phe Leu Arg Leu Met Ser Thr Glu
        195                 200                 205

Ala Ser Gln Asn Ile Thr Tyr His Cys Lys Asn Ser Val Ala Tyr Met
    210                 215                 220

Asp Gln Gln Thr Gly Asn Leu Lys Lys Ala Leu Leu Leu Lys Gly Ser
225                 230                 235                 240

Asn Glu Ile Glu Ile Arg Ala Glu Gly Asn Ser Arg Phe Thr Tyr Ser
                245                 250                 255

Val Thr Val Asp Gly Cys Thr Ser His Thr Gly Ala Trp Gly Lys Thr
            260                 265                 270

Val Ile Glu Tyr Lys Thr Thr Lys Ser Ser Arg Leu Pro Ile Ile Asp
        275                 280                 285

Val Ala Pro Leu Asp Val Gly Ala Pro Asp Gln Glu Phe Gly Phe Asp
    290                 295                 300
```

Val Gly Pro Val Cys Phe Leu
305                 310

<210> SEQ ID NO 3
<211> LENGTH: 771
<212> TYPE: DNA
<213> ORGANISM: Homo sapiens
<220> FEATURE:
<221> NAME/KEY: CDS
<222> LOCATION: (12)...(755)

<400> SEQUENCE: 3

| | | | | | |
|---|---|---|---|---|---|
| aagcttacgt | aagatctgat | gccaatgtgg | ttcgtgaccg | tgacctcgag | gtggacacca | 60 |
| ccctcaagag | cctgagccag | cagatcgaga | acatccggag | cccagaggga | agccgcaaga | 120 |
| accccgcccg | cacctgccgt | gacctcaaga | tgtgccactc | tgactggaag | agtggagagt | 180 |
| actggattga | ccccaaccaa | ggctgcaacc | tggatgccat | caaagtcttc | tgcaacatgg | 240 |
| agactggtga | gacctgcgtg | taccccactc | agcccagtgt | ggcccagaag | aactggtaca | 300 |
| tcagcaagaa | ccccaaggac | aagaggcatg | tctggttcgg | cgagagcatg | accgatggat | 360 |
| tccagttcga | gtatggcggc | cagggctccg | accctgccga | tgtggccatc | cagctgacct | 420 |
| tcctgcgcct | gatgtccacc | gaggcctccc | agaacatcac | ctaccactgc | aagaacagcg | 480 |
| tggcctacat | ggaccagcag | actggcaacc | tcaagaaggc | cctgctcctc | aagggctcca | 540 |
| acgagatcga | gatccgcgcc | gagggcaaca | gccgcttcac | ctacagcgtc | actgtcgatg | 600 |
| gctgcacgag | tcacaccgga | gcctggggca | agacagtgat | tgaatacaaa | accaccaagt | 660 |
| cctcccgcct | gcccatcatc | gatgtggccc | ccttggacgt | tggtgcccca | gaccaggaat | 720 |
| tcggcttcga | cgttggccct | gtctgcttcc | tgtaaactcc | ctccatctag | a | 771 |

<210> SEQ ID NO 4
<211> LENGTH: 247
<212> TYPE: PRT
<213> ORGANISM: Homo sapiens

<400> SEQUENCE: 4

Arg Ser Asp Ala Asn Val Val Arg Asp Arg Asp Leu Glu Val Asp Thr
1               5                   10                  15

Thr Leu Lys Ser Leu Ser Gln Gln Ile Glu Asn Ile Arg Ser Pro Glu
            20                  25                  30

Gly Ser Arg Lys Asn Pro Ala Arg Thr Cys Arg Asp Leu Lys Met Cys
        35                  40                  45

His Ser Asp Trp Lys Ser Gly Glu Tyr Trp Ile Asp Pro Asn Gln Gly
    50                  55                  60

Cys Asn Leu Asp Ala Ile Lys Val Phe Cys Asn Met Glu Thr Gly Glu
65                  70                  75                  80

Thr Cys Val Tyr Pro Thr Gln Pro Ser Val Ala Gln Lys Asn Trp Tyr
                85                  90                  95

Ile Ser Lys Asn Pro Lys Asp Lys Arg His Val Trp Phe Gly Glu Ser
            100                 105                 110

Met Thr Asp Gly Phe Gln Phe Glu Tyr Gly Gly Gln Gly Ser Asp Pro
        115                 120                 125

Ala Asp Val Ala Ile Gln Leu Thr Phe Leu Arg Leu Met Ser Thr Glu
    130                 135                 140

Ala Ser Gln Asn Ile Thr Tyr His Cys Lys Asn Ser Val Ala Tyr Met
145                 150                 155                 160

```
Asp Gln Gln Thr Gly Asn Leu Lys Lys Ala Leu Leu Lys Gly Ser
            165                 170                 175

Asn Glu Ile Glu Ile Arg Ala Glu Gly Asn Ser Arg Phe Thr Tyr Ser
        180                 185                 190

Val Thr Val Asp Gly Cys Thr Ser His Thr Gly Ala Trp Gly Lys Thr
        195                 200                 205

Val Ile Glu Tyr Lys Thr Thr Lys Ser Ser Arg Leu Pro Ile Ile Asp
    210                 215                 220

Val Ala Pro Leu Asp Val Gly Ala Pro Asp Gln Glu Phe Gly Phe Asp
225                 230                 235                 240

Val Gly Pro Val Cys Phe Leu
                245

<210> SEQ ID NO 5
<211> LENGTH: 2487
<212> TYPE: DNA
<213> ORGANISM: Homo sapiens
<220> FEATURE:
<221> NAME/KEY: CDS
<222> LOCATION: (12)...(2471)

<400> SEQUENCE: 5
aagcttcctg catgctgctg ctgctgctgc tgctgggcct gaggctacag ctctccctgg      60
gcatcatccc agttgaggag gagaacccgg acttctggaa ccgcgaggca gccgaggccc     120
tgggtgccgc caagaagctg cagcctgcac agacagccgc caagaacctc atcatcttcc     180
tgggcgatgg gatgggggtg tctacggtga cagctgccag gatcctaaaa gggcagaaga     240
aggacaaact ggggcctgag ataccCctgg ccatggaccg cttcccatat gtggctctgt     300
ccaagacata caatgtagac aaacatgtgc cagacagtgg agccacagcc acggcctacc     360
tgtgcggggt caagggcaac ttccagacca ttggcttgag tgcagccgcc cgctttaacc     420
agtgcaacac gacacgcggc aacgaggtca tctccgtgat gaatcgggcc aagaaagcag     480
ggaagtcagt gggagtggta accaccacac gagtgcagca cgcctcgcca gccggcacct     540
acgcccacac ggtgaaccgc aactggtact cggacgccga cgtgcctgcc tcggcccgcc     600
aggagggtgt ccaggacatc gctacgcagc tcatctccaa catggacatt gacgtgatcc     660
taggtggagg ccgaaagtac atgtttccca tgggaacccc agaccctgag tacccagatg     720
actacagcca aggtgggacc aggctggacg ggaagaatct ggtgcaggaa tggctggcga     780
agcgccaggg tgcccggtat gtgtggaacc gcactgagct catgcaggct ccctggacc     840 cgtctgtgac ccatctcatg ggtctctttg agcctggaga catgaaatac gagatccacc     900
gagactccac actggacccc tccctgatgg agatgacaga ggctgccctg cgcctgctga     960
gcaggaaccc ccgcggcttc ttcctcttcg tggagggtgg tcgcatcgac catggtcatc    1020
atgaaagcag ggcttaccgg gcactgactg agacgatcat gttcgacgac gccattgaga    1080
gggcgggcca gctcaccagc gaggaggaca cgctgagcct cgtcactgcc gaccactccc    1140
acgtcttctc cttcggaggc taccccctgc gagggagctc catcttcggg ctggcccctg    1200
gcaaggcccg ggacaggaag gcctacacgg tcctcctata cggaaacggt ccaggctatg    1260
tgctcaagga cggcgcccgg ccggatgtta ccgagagcga gagcgggagc ccgagtatc    1320 ggcagcagtc agcagtgccc ctggacgaag agacccacgc aggcgaggac gtggcggtgt    1380
tcgcgcgcgg cccgcaggcg cacctggttc acggcgtgca ggagcagacc ttcatagcgc    1440
acgtcatggc cttcgccgcc tgcctggagc cctacaccgc ctgcgacctg gcgccccccg    1500
```

-continued

```
ccggcaccac cgacgccgcg cacccgggtt ccggaagatc taacggtctc cctggcccca   1560
ttgggccccc tggtcctcgc ggtcgcactg gtgatgctgg tcctgttggt cccccggcc    1620 ctcctggacc tcctggtccc cctggtcctc ccagcgctgg tttcgacttc agcttcctgc   1680
cccagccacc tcaagagaag gctcacgatg gtggccgcta ctaccgggct gatgatgcca   1740
atgtggttcg tgaccgtgac ctcgaggtgg acaccaccct caagagcctg agccagcaga   1800
tcgagaacat ccggagccca gagggaagcc gcaagaaccc cgcccgcacc tgccgtgacc   1860
tcaagatgtg ccactctgac tggaagagtg gagagtactg gattgacccc aaccaaggct   1920
gcaacctgga tgccatcaaa gtcttctgca acatggagac tggtgagacc tgcgtgtacc   1980
ccactcagcc cagtgtggcc cagaagaact ggtacatcag caagaacccc aaggacaaga   2040
ggcatgtctg gttcggcgag agcatgaccg atggattcca gttcgagtat ggcggccagg   2100
gctccgaccc tgccgatgtg gccatccagc tgaccttcct gcgcctgatg tccaccgagg   2160
cctcccagaa catcacctac cactgcaaga acagcgtggc ctacatggac agcagactg    2220 gcaacctcaa gaaggccctg ctcctcaagg gctccaacga gatcgagatc cgcgccgagg   2280
gcaacagccg cttcacctac agcgtcactg tcgatggctg cacgagtcac accggagcct   2340
ggggcaagac agtgattgaa tacaaaaacca ccaagtcctc ccgcctgccc atcatcgatg   2400
tggccccctt ggacgttggt gccccagacc aggaattcgg cttcgacgtt ggccctgtct   2460
gcttcctgta aactccctcc atctaga                                       2487

<210> SEQ ID NO 6
<211> LENGTH: 819
<212> TYPE: PRT
<213> ORGANISM: Homo sapiens

<400> SEQUENCE: 6

Met Leu Leu Leu Leu Leu Leu Gly Leu Arg Leu Gln Leu Ser Leu
                 5                  10                  15

Gly Ile Ile Pro Val Glu Glu Glu Asn Pro Asp Phe Trp Asn Arg Glu
                20                  25                  30

Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
        50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
```

-continued

```
            195                 200                 205
Ser Asn Met Asp Ile Asp Val Ile Leu Gly Gly Arg Lys Tyr Met
210                 215                 220

Phe Pro Met Gly Thr Pro Asp Pro Glu Tyr Pro Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
                260                 265                 270

Ala Ser Leu Asp Pro Ser Val Thr His Leu Met Gly Leu Phe Glu Pro
        275                 280                 285

Gly Asp Met Lys Tyr Glu Ile His Arg Asp Ser Thr Leu Asp Pro Ser
        290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
                340                 345                 350

Asp Ala Ile Glu Arg Ala Gly Gln Leu Thr Ser Glu Glu Asp Thr Leu
                355                 360                 365

Ser Leu Val Thr Ala Asp His Ser His Val Phe Ser Phe Gly Gly Tyr
        370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
                420                 425                 430

Ser Pro Glu Tyr Arg Gln Gln Ser Ala Val Pro Leu Asp Glu Glu Thr
        435                 440                 445

His Ala Gly Glu Asp Val Ala Val Phe Ala Arg Gly Pro Gln Ala His
        450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Ser Gly Arg Ser Asn Gly
                500                 505                 510

Leu Pro Gly Pro Ile Gly Pro Gly Pro Arg Gly Arg Thr Gly Asp
        515                 520                 525

Ala Gly Pro Val Gly Pro Pro Gly Pro Pro Gly Pro Pro Gly Pro Pro
        530                 535                 540

Gly Pro Pro Ser Ala Gly Phe Asp Phe Ser Phe Leu Pro Gln Pro Pro
545                 550                 555                 560

Gln Glu Lys Ala His Asp Gly Arg Tyr Tyr Arg Ala Asp Asp Ala
                565                 570                 575

Asn Val Val Arg Asp Arg Asp Leu Glu Val Asp Thr Thr Leu Lys Ser
                580                 585                 590

Leu Ser Gln Gln Ile Glu Asn Ile Arg Ser Pro Glu Gly Ser Arg Lys
        595                 600                 605

Asn Pro Ala Arg Thr Cys Arg Asp Leu Lys Met Cys His Ser Asp Trp
610                 615                 620
```

```
Lys Ser Gly Glu Tyr Trp Ile Asp Pro Asn Gln Gly Cys Asn Leu Asp
625                 630                 635                 640

Ala Ile Lys Val Phe Cys Asn Met Glu Thr Gly Glu Thr Cys Val Tyr
            645                 650                 655

Pro Thr Gln Pro Ser Val Ala Gln Lys Asn Trp Tyr Ile Ser Lys Asn
        660                 665                 670

Pro Lys Asp Lys Arg His Val Trp Phe Gly Ser Met Thr Asp Gly
    675                 680                 685

Phe Gln Phe Glu Tyr Gly Gly Gln Gly Ser Asp Pro Ala Asp Val Ala
    690                 695                 700

Ile Gln Leu Thr Phe Leu Arg Leu Met Ser Thr Glu Ala Ser Gln Asn
705                 710                 715                 720

Ile Thr Tyr His Cys Lys Asn Ser Val Ala Tyr Met Asp Gln Gln Thr
                725                 730                 735

Gly Asn Leu Lys Lys Ala Leu Leu Leu Lys Gly Ser Asn Glu Ile Glu
            740                 745                 750

Ile Arg Ala Glu Gly Asn Ser Arg Phe Thr Tyr Ser Val Thr Val Asp
755                 760                 765

Gly Cys Thr Ser His Thr Gly Ala Trp Gly Lys Thr Val Ile Glu Tyr
770                 775                 780

Lys Thr Thr Lys Ser Ser Arg Leu Pro Ile Ile Asp Val Ala Pro Leu
785                 790                 795                 800

Asp Val Gly Ala Pro Asp Gln Glu Phe Gly Phe Asp Val Gly Pro Val
                805                 810                 815

Cys Phe Leu
        819

<210> SEQ ID NO 7
<211> LENGTH: 2294
<212> TYPE: DNA
<213> ORGANISM: Homo sapiens
<220> FEATURE:
<221> NAME/KEY: CDS
<222> LOCATION: (12)...(2278)

<400> SEQUENCE: 7
aagcttcctg catgctgctg ctgctgctgc tgctgggcct gaggctacag ctctccctgg    60
gcatcatccc agttgaggag gagaacccgg acttctggaa ccgcgaggca gccgaggccc   120
tgggtgccgc caagaagctg cagcctgcac agacagccgc caagaacctc atcatcttcc   180
tgggcgatgg gatgggggtg tctacggtga cagctgccag gatcctaaaa gggcagaaga   240
aggacaaact gggcctgag ataccctgg ccatggaccg cttcccatat gtggctctgt    300
ccaagacata caatgtagac aaacatgtgc agacagtgg agccacagcc acggcctacc    360 tgtgcgggt caagggcaac ttccagacca ttggcttgag tgcagccgcc cgctttaacc    420
agtgcaacac gacacgcggc aacgaggtca tctccgtgat gaatcgggcc aagaaagcag    480
ggaagtcagt gggagtggta accaccacac gagtgcagca cgcctcgcca gccggcacct    540
acgcccacac ggtgaaccgc aactggtact cggacgccga cgtgcctgcc tcggcccgcc   600 aggagggtg ccaggacatc gctacgcagc tcatctccaa catggacatt gacgtgatcc    660
taggtggagg ccgaaagtac atgtttccca tgggaacccc agaccctgag tacccagatg    720
actacagcca aggtgggacc aggctggacg ggaagaatct ggtgcaggaa tggctggcga    780
agcgccaggg tgcccggtat gtgtggaacc gcactgagct catgcaggct tccctggacc    840
```

```
cgtctgtgac ccatctcatg ggtctctttg agcctggaga catgaaatac gagatccacc     900
gagactccac actggacccc tccctgatgg agatgacaga ggctgccctg cgcctgctga     960
gcaggaaccc ccgcggcttc ttcctcttcg tggagggtgg tcgcatcgac catggtcatc    1020
atgaaagcag ggcttaccgg gcactgactg agacgatcat gttcgacgac gccattgaga    1080
gggcgggcca gctcaccagc gaggaggaca cgctgagcct cgtcactgcc gaccactccc    1140
acgtcttctc cttcggaggc tacccctgc gagggagctc catcttcggg ctggcccctg    1200
gcaaggcccg ggacaggaag gcctacacgg tcctcctata cggaaacggt ccaggctatg    1260
tgctcaagga cggcgcccgg ccggatgtta ccgagcgcga gagcgggagc ccgagtatc    1320
ggcagcagtc agcagtgccc ctggacgaag agacccacgc aggcgaggac gtggcggtgt    1380
tcgcgcgcgg cccgcaggcg cacctggttc acggcgtgca ggagcagacc ttcatagcgc    1440
acgtcatggc cttcgccgcc tgcctggagc cctacaccgc ctgcgacctg cgcccccccg    1500
ccggcaccac cgacgccgcg cacccgggtt ccggagatct gatgccaatg tggttcgtga    1560
ccgtgacctc gaggtggaca ccaccctcaa gagcctgagc cagcagatcg agaacatccg    1620
gagcccagag ggaagccgca agaaccccgc ccgcacctgc cgtgacctca agatgtgcca    1680
ctctgactgg aagagtggag agtactggat tgaccccaac caaggctgca acctggatgc    1740
catcaaagtc ttctgcaaca tggagactgg tgagacctgc gtgtacccca ctcagcccag    1800
tgtggcccag aagaactggt acatcagcaa gaaccccaag gacaagaggc atgtctggtt    1860
cggcgagagc atgaccgatg gattccagtt cgagtatggc ggccagggct ccgaccctgc    1920
cgatgtggcc atccagctga ccttcctgcg cctgatgtcc accgaggcct cccagaacat    1980
cacctaccac tgcaagaaca gcgtggccta catggaccag cagactgcaa acctcaagaa    2040
ggccctgctc ctcaagggct ccaacgagat cgagatccgc gccgagggca acagccgctt    2100
cacctacagc gtcactgtcg atggctgcac gagtcacacc ggagcctggg caagacagt    2160
gattgaatac aaaaccacca gtcctcccg cctgcccatc atcgatgtgg ccccttgga    2220
cgttggtgcc ccagaccagg aattcggctt cgacgttggc cctgtctgct tcctgtaaac    2280
tccctccatc taga                                                      2294
```

<210> SEQ ID NO 8
<211> LENGTH: 755
<212> TYPE: PRT
<213> ORGANISM: Homo sapiens

<400> SEQUENCE: 8

```
Met Leu Leu Leu Leu Leu Leu Gly Leu Arg Leu Gln Leu Ser Leu
1               5                   10                  15

Gly Ile Ile Pro Val Glu Glu Glu Asn Pro Asp Phe Trp Asn Arg Glu
                20                  25                  30

Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
        50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110
```

```
Ala Thr Ala Tyr Leu Cys Gly Val Lys Gly Asn Phe Gln Thr Ile Gly
            115                 120                 125

Leu Ser Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
            195                 200                 205

Ser Asn Met Asp Ile Asp Val Ile Leu Gly Gly Arg Lys Tyr Met
    210                 215                 220

Phe Pro Met Gly Thr Pro Asp Pro Glu Tyr Pro Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
            260                 265                 270

Ala Ser Leu Asp Pro Ser Val Thr His Leu Met Gly Leu Phe Glu Pro
            275                 280                 285

Gly Asp Met Lys Tyr Glu Ile His Arg Asp Ser Thr Leu Asp Pro Ser
    290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
            355                 360                 365

Ser Leu Val Thr Ala Asp His Ser His Val Phe Ser Phe Gly Gly Tyr
    370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
            405                 410                 415

Val Leu Lys Asp Gly Ala Arg Pro Asp Val Thr Glu Ser Glu Ser Gly
            420                 425                 430

Ser Pro Glu Tyr Arg Gln Gln Ser Ala Val Pro Leu Asp Glu Glu Thr
    435                 440                 445

His Ala Gly Glu Asp Val Ala Val Phe Ala Arg Gly Pro Gln Ala His
    450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Ser Gly Arg Ser Asp Ala
            500                 505                 510

Asn Val Val Arg Asp Arg Asp Leu Glu Val Asp Thr Thr Leu Lys Ser
            515                 520                 525

Leu Ser Gln Gln Ile Glu Asn Ile Arg Ser Pro Glu Gly Ser Arg Lys
```

| | | | | | | | | | | | | |
|---|---|---|---|---|---|---|---|---|---|---|---|---|
| | | | 530 | | | 535 | | | 540 | | | |
| Asn | Pro | Ala | Arg | Thr | Cys | Arg | Asp | Leu | Lys | Met | Cys | His | Ser | Asp | Trp |
| 545 | | | | | 550 | | | | | 555 | | | | | 560 |
| Lys | Ser | Gly | Glu | Tyr | Trp | Ile | Asp | Pro | Asn | Gln | Gly | Cys | Asn | Leu | Asp |
| | | | | 565 | | | | | 570 | | | | | 575 | |
| Ala | Ile | Lys | Val | Phe | Cys | Asn | Met | Glu | Thr | Gly | Glu | Thr | Cys | Val | Tyr |
| | | | 580 | | | | | 585 | | | | | 590 | | |
| Pro | Thr | Gln | Pro | Ser | Val | Ala | Gln | Lys | Asn | Trp | Tyr | Ile | Ser | Lys | Asn |
| | | 595 | | | | | 600 | | | | | 605 | | | |
| Pro | Lys | Asp | Lys | Arg | His | Val | Trp | Phe | Gly | Ser | Met | Thr | Asp | Gly | |
| | 610 | | | | | 615 | | | | | 620 | | | | |
| Phe | Gln | Phe | Glu | Tyr | Gly | Gly | Gln | Gly | Ser | Asp | Pro | Ala | Asp | Val | Ala |
| 625 | | | | | 630 | | | | | 635 | | | | | 640 |
| Ile | Gln | Leu | Thr | Phe | Leu | Arg | Leu | Met | Ser | Thr | Glu | Ala | Ser | Gln | Asn |
| | | | | 645 | | | | | 650 | | | | | 655 | |
| Ile | Thr | Tyr | His | Cys | Lys | Asn | Ser | Val | Ala | Tyr | Met | Asp | Gln | Gln | Thr |
| | | | 660 | | | | | 665 | | | | | 670 | | |
| Gly | Asn | Leu | Lys | Lys | Ala | Leu | Leu | Leu | Lys | Gly | Ser | Asn | Glu | Ile | Glu |
| | | 675 | | | | | 680 | | | | | 685 | | | |
| Ile | Arg | Ala | Glu | Gly | Asn | Ser | Arg | Phe | Thr | Tyr | Ser | Val | Thr | Val | Asp |
| | 690 | | | | | 695 | | | | | 700 | | | | |
| Gly | Cys | Thr | Ser | His | Thr | Gly | Ala | Trp | Gly | Lys | Thr | Val | Ile | Glu | Tyr |
| 705 | | | | | 710 | | | | | 715 | | | | | 720 |
| Lys | Thr | Thr | Lys | Ser | Ser | Arg | Leu | Pro | Ile | Ile | Asp | Val | Ala | Pro | Leu |
| | | | | 725 | | | | | 730 | | | | | 735 | |
| Asp | Val | Gly | Ala | Pro | Asp | Gln | Glu | Phe | Gly | Phe | Asp | Val | Gly | Pro | Val |
| | | | 740 | | | | | 745 | | | | | 750 | | |
| Cys | Phe | Leu | | | | | | | | | | | | | |
| | | 755 | | | | | | | | | | | | | |

```
<210> SEQ ID NO 9
<211> LENGTH: 1734
<212> TYPE: DNA
<213> ORGANISM: Homo sapiens
<220> FEATURE:
<221> NAME/KEY: CDS
<222> LOCATION: (18)...(1718)

<400> SEQUENCE: 9
ggatcccgcc cgcacccatg gcgcccgtcg ccgtctgggc cgcgctggcc gtcggactgg      60
agctctgggc tgcggcgcac gccttgcccg cccaggtggc atttacaccc tacgccccgg     120
agcccgggag cacatgccgg ctcagagaat actatgacca cagctcag atgtgctgca     180 gcaaatgctc gccgggccaa catgcaaaag tcttctgtac caagacctcg dacaccgtgt     240
gtgactcctg tgaggacagc acatacaccc agctctggaa ctgggttccc gagtgcttga     300
gctgtggctc ccgctgtagc tctgaccagg tggaaactca agcctgcact cgggaacaga     360
accgcatctg cacctgcagg cccggctggt actgcgcgct gagcaagcag agggggtgcc     420
ggctgtgcgc gccgctgcgc aagtgccgcc cgggcttcgg cgtggccaga ccaggaactg     480
aaacatcaga cgtggtgtgc aagccctgtg ccccggggac gttctccaac acgacttcat     540
ccacggatat ttgcaggccc caccagatct gtaacgtggt ggccatccct gggaatgcaa     600
gcatggatgc agtctgcacg tccacgtccc cacccggag tatggcccca ggggcagtac     660
acttacccca gccagtgtcc acgcgatccc aacacacgca gccaactcca gaacccagca     720
```

-continued

```
ctgctccaag cacctccttc ctgctcccaa tgggccccag cccccagct gaagggagca      780
ctggatctaa cggtctccct ggccccattg gccccctgg tcctcgcggt cgcactggtg      840
atgctggtcc tgttggtccc cccggccctc ctggacctcc tggtccccct ggtcctccca    900
gcgctggttt cgacttcagc ttcctgcccc agccacctca agagaaggct cacgatggtg    960
gccgctacta ccgggctgat gatgccaatg tggttcgtga ccgtgacctc gaggtggaca   1020
ccaccctcaa gagcctgagc cagcagatcg agaacatccg gagcccagag gaagccgca    1080
agaaccccgc ccgcacctgc cgtgacctca gatgtgccca ctctgactgg aagagtggag   1140
agtactggat tgaccccaac caaggctgca acctggatgc catcaaagtc ttctgcaaca   1200
tggagactgg tgagacctgc gtgtacccca ctcagcccag tgtggcccag aagaactggt   1260
acatcagcaa gaaccccaag gacaagaggc atgtctggtt cggcgagagc atgaccgatg   1320
gattccagtt cgagtatggc ggccagggct ccgaccctgc cgatgtggcc atccagctga   1380
ccttcctgcg cctgatgtcc accgaggcct cccagaacat cacctaccac tgcaagaaca   1440
gcgtggccta catggaccag cagactggca acctcaagaa ggccctgctc ctcaagggct   1500
ccaacgagat cgagatccgc gccgagggca cagccgctt cacctacagc gtcactgtcg    1560
atggctgcac gagtcacacc ggagcctggg gcaagacagt gattgaatac aaaaccacca   1620
agtcctcccg cctgcccatc atcgatgtgg cccccttgga cgttggtgcc ccagaccagg   1680
aattcggctt cgacgttggc cctgtctgct tcctgtaaac tccctccatc taga         1734
```

<210> SEQ ID NO 10
<211> LENGTH: 566
<212> TYPE: PRT
<213> ORGANISM: Homo sapiens

<400> SEQUENCE: 10

```
Met Ala Pro Val Ala Val Trp Ala Ala Leu Ala Val Gly Leu Glu Leu
              5                   10                  15
Trp Ala Ala Ala His Ala Leu Pro Ala Gln Val Ala Phe Thr Pro Tyr
         20                  25                  30
Ala Pro Glu Pro Gly Ser Thr Cys Arg Leu Arg Glu Tyr Tyr Asp Gln
     35                  40                  45
Thr Ala Gln Met Cys Cys Ser Lys Cys Ser Pro Gly Gln His Ala Lys
 50                  55                  60
Val Phe Cys Thr Lys Thr Ser Asp Thr Val Cys Asp Ser Cys Glu Asp
 65                  70                  75                  80
Ser Thr Tyr Thr Gln Leu Trp Asn Trp Val Pro Glu Cys Leu Ser Cys
             85                  90                  95
Gly Ser Arg Cys Ser Ser Asp Gln Val Glu Thr Gln Ala Cys Thr Arg
         100                 105                 110
Glu Gln Asn Arg Ile Cys Thr Cys Arg Pro Gly Trp Tyr Cys Ala Leu
     115                 120                 125
Ser Lys Gln Glu Gly Cys Arg Leu Cys Ala Pro Leu Arg Lys Cys Arg
130                 135                 140
Pro Gly Phe Gly Val Ala Arg Pro Gly Thr Glu Thr Ser Asp Val Val
145                 150                 155                 160
Cys Lys Pro Cys Ala Pro Gly Thr Phe Ser Asn Thr Thr Ser Ser Thr
             165                 170                 175
Asp Ile Cys Arg Pro His Gln Ile Cys Asn Val Val Ala Ile Pro Gly
         180                 185                 190
Asn Ala Ser Met Asp Ala Val Cys Thr Ser Thr Ser Pro Thr Arg Ser
```

195                 200                 205
Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Ser Asn Gly Leu Pro Gly Pro Ile Gly Pro Pro Gly Pro Arg Gly Arg
                260                 265                 270

Thr Gly Asp Ala Gly Pro Val Gly Pro Pro Gly Pro Gly Pro Pro
            275                 280                 285

Gly Pro Pro Gly Pro Ser Ala Gly Phe Asp Phe Ser Phe Leu Pro
290                 295                 300

Gln Pro Pro Gln Glu Lys Ala His Asp Gly Arg Tyr Tyr Arg Ala
305                 310                 315                 320

Asp Asp Ala Asn Val Val Arg Asp Arg Asp Leu Glu Val Asp Thr Thr
                325                 330                 335

Leu Lys Ser Leu Ser Gln Gln Ile Glu Asn Ile Arg Ser Pro Glu Gly
                340                 345                 350

Ser Arg Lys Asn Pro Ala Arg Thr Cys Arg Asp Leu Lys Met Cys His
            355                 360                 365

Ser Asp Trp Lys Ser Gly Glu Tyr Trp Ile Asp Pro Asn Gln Gly Cys
370                 375                 380

Asn Leu Asp Ala Ile Lys Val Phe Cys Asn Met Glu Thr Gly Glu Thr
385                 390                 395                 400

Cys Val Tyr Pro Thr Gln Pro Ser Val Ala Gln Lys Asn Trp Tyr Ile
                405                 410                 415

Ser Lys Asn Pro Lys Asp Lys Arg His Val Trp Phe Gly Glu Ser Met
                420                 425                 430

Thr Asp Gly Phe Gln Phe Glu Tyr Gly Gly Gln Gly Ser Asp Pro Ala
            435                 440                 445

Asp Val Ala Ile Gln Leu Thr Phe Leu Arg Leu Met Ser Thr Glu Ala
450                 455                 460

Ser Gln Asn Ile Thr Tyr His Cys Lys Asn Ser Val Ala Tyr Met Asp
465                 470                 475                 480

Gln Gln Thr Gly Asn Leu Lys Lys Ala Leu Leu Leu Lys Gly Ser Asn
                485                 490                 495

Glu Ile Glu Ile Arg Ala Glu Gly Asn Ser Arg Phe Thr Tyr Ser Val
            500                 505                 510

Thr Val Asp Gly Cys Thr Ser His Thr Gly Ala Trp Gly Lys Thr Val
            515                 520                 525

Ile Glu Tyr Lys Thr Thr Lys Ser Ser Arg Leu Pro Ile Ile Asp Val
            530                 535                 540

Ala Pro Leu Asp Val Gly Ala Pro Asp Gln Glu Phe Gly Phe Asp Val
545                 550                 555                 560

Gly Pro Val Cys Phe Leu
                565

<210> SEQ ID NO 11
<211> LENGTH: 1542
<212> TYPE: DNA
<213> ORGANISM: Homo sapiens
<220> FEATURE:
<221> NAME/KEY: CDS
<222> LOCATION: (18)...(1526)

<400> SEQUENCE: 11

```
ggatcccgcc cgcacccatg gcgcccgtcg ccgtctgggc cgcgctggcc gtcggactgg      60
agctctgggc tgcggcgcac gccttgcccg cccaggtggc atttacaccc tacgccccgg     120
agcccgggag cacatgccgg ctcagagaat actatgacca gacagctcag atgtgctgca     180
gcaaatgctc gccgggccaa catgcaaaag tcttctgtac aagacctcg gacaccgtgt      240
gtgactcctg tgaggacagc acatacaccc agctctggaa ctgggttccc gagtgcttga     300
gctgtggctc ccgctgtagc tctgaccagg tggaaactca agcctgcact cgggaacaga     360
accgcatctg cacctgcagg cccggctggt actgcgcgct gagcaagcag gagggtgcc      420
ggctgtgcgc gccgctgcgc aagtgccgcc gggcttcgg cgtggccaga ccaggaactg      480
aaacatcaga cgtggtgtgc aagccctgtg ccccggggac gttctccaac acgacttcat     540
ccacggatat ttgcaggccc caccagatct gtaacgtggt ggccatccct gggaatgcaa     600
gcatggatgc agtctgcacg tccacgtccc ccaccccgag tatggcccca ggggcagtac     660
acttaccccca gccagtgtcc acacgatccc aacacacgca gccaactcca gaacccagca     720
ctgctccaag cacctccttc ctgctcccaa tgggccccag ccccccagct gaagggagca     780
ctggatctga tgccaatgtg gttcgtgacc gtgacctcga ggtggacacc accctcaaga     840
gcctgagcca gcagatcgag aacatccgga gcccagaggg aagccgcaag aaccccgccc     900
gcacctgccg tgacctcaag atgtgccact ctgactggaa gagtgagag tactggattg      960
acccccaacca aggctgcaac ctggatgcca tcaaagtctt ctgcaacatg gagactggtg    1020
agacctgcgt gtaccccact cagcccagtg tgcccagaa gaactggtac atcagcaaga     1080
acccccaagga caagaggcat gtctggttcg gcgagagcat gaccgatgga ttccagttcg    1140
agtatggcgg ccagggctcc gaccctgccg atgtggccat ccagctgacc ttcctgcgcc    1200
tgatgtccac cgaggcctcc cagaacatca cctaccactg caagaacagc gtggcctaca    1260
tggaccagca gactggcaac ctcaagaagg ccctgctcct caagggctcc aacgagatcg    1320
agatccgcgc cgagggcaac agccgcttca cctacagcgt cactgtcgat ggctgcacga    1380
gtcacaccgg agcctggggc aagacagtga ttgaatacaa aaccaccaag tcctcccgcc    1440
tgccccatcat cgatgtggcc cccttggacg ttggtgcccc agaccaggaa ttcggcttcg    1500
acgttggccc tgtctgcttc ctgtaaactc cctccatcta ga                       1542
```

<210> SEQ ID NO 12
<211> LENGTH: 502
<212> TYPE: PRT
<213> ORGANISM: Homo sapiens

<400> SEQUENCE: 12

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
```

```
                    85                  90                  95
Gly Ser Arg Cys Ser Ser Asp Gln Val Glu Thr Gln Ala Cys Thr Arg
                100                 105                 110
Glu Gln Asn Arg Ile Cys Thr Cys Arg Pro Gly Trp Tyr Cys Ala Leu
                115                 120                 125
Ser Lys Gln Glu Gly Cys Arg Leu Cys Ala Pro Leu Arg Lys Cys Arg
        130                 135                 140
Pro Gly Phe Gly Val Ala Arg Pro Gly Thr Glu Thr Ser Asp Val Val
145                 150                 155                 160
Cys Lys Pro Cys Ala Pro Gly Thr Phe Ser Asn Thr Thr Ser Ser Thr
                165                 170                 175
Asp Ile Cys Arg Pro His Gln Ile Cys Asn Val Val Ala Ile Pro Gly
            180                 185                 190
Asn Ala Ser Met Asp Ala Val Cys Thr Ser Thr Ser Pro Thr Arg Ser
            195                 200                 205
Met Ala Pro Gly Ala Val His Leu Pro Gln Pro Val Ser Thr Arg Ser
        210                 215                 220
Gln His Thr Gln Pro Thr Pro Glu Pro Ser Thr Ala Pro Ser Thr Ser
225                 230                 235                 240
Phe Leu Leu Pro Met Gly Pro Ser Pro Ala Glu Gly Ser Thr Gly
                245                 250                 255
Ser Asp Ala Asn Val Val Arg Asp Arg Asp Leu Glu Val Asp Thr Thr
            260                 265                 270
Leu Lys Ser Leu Ser Gln Gln Ile Glu Asn Ile Arg Ser Pro Glu Gly
        275                 280                 285
Ser Arg Lys Asn Pro Ala Arg Thr Cys Arg Asp Leu Lys Met Cys His
        290                 295                 300
Ser Asp Trp Lys Ser Gly Glu Tyr Trp Ile Asp Pro Asn Gln Gly Cys
305                 310                 315                 320
Asn Leu Asp Ala Ile Lys Val Phe Cys Asn Met Glu Thr Gly Glu Thr
                325                 330                 335
Cys Val Tyr Pro Thr Gln Pro Ser Val Ala Gln Lys Asn Trp Tyr Ile
                340                 345                 350
Ser Lys Asn Pro Lys Asp Lys Arg His Val Trp Phe Gly Glu Ser Met
            355                 360                 365
Thr Asp Gly Phe Gln Phe Glu Tyr Gly Gly Gln Gly Ser Asp Pro Ala
        370                 375                 380
Asp Val Ala Ile Gln Leu Thr Phe Leu Arg Leu Met Ser Thr Glu Ala
385                 390                 395                 400
Ser Gln Asn Ile Thr Tyr His Cys Lys Asn Ser Val Ala Tyr Met Asp
                405                 410                 415
Gln Gln Thr Gly Asn Leu Lys Lys Ala Leu Leu Leu Lys Gly Ser Asn
            420                 425                 430
Glu Ile Glu Ile Arg Ala Glu Gly Asn Ser Arg Phe Thr Tyr Ser Val
            435                 440                 445
Thr Val Asp Gly Cys Thr Ser His Thr Gly Ala Trp Gly Lys Thr Val
        450                 455                 460
Ile Glu Tyr Lys Thr Thr Lys Ser Ser Arg Leu Pro Ile Ile Asp Val
465                 470                 475                 480
Ala Pro Leu Asp Val Gly Ala Pro Asp Gln Glu Phe Gly Phe Asp Val
                485                 490                 495
Gly Pro Val Cys Phe Leu
                500
```

-continued

<210> SEQ ID NO 13
<211> LENGTH: 2139
<212> TYPE: DNA
<213> ORGANISM: Homo sapiens
<220> FEATURE:
<221> NAME/KEY: CDS
<222> LOCATION: (24)...(2123)

<400> SEQUENCE: 13

| | | | | | |
|---|---|---|---|---|---|
| aagcttccct | cggcaaggcc | acaatgaacc | ggggagtccc | ttttaggcac | ttgcttctgg | 60 |
| tgctgcaact | ggcgctcctc | ccagcagcca | ctcaggaaaa | gaaagtggtg | ctgggcaaaa | 120 |
| aaggggatac | agtggaactg | acctgtacag | cttcccagaa | gagagcata | caattccact | 180 |
| ggaaaaactc | caaccagata | aagattctgg | gaaatcaggg | ctccttctta | actaaaggtc | 240 |
| catccaagct | gaatgatcgc | gctgactcaa | gaagaagcct | tgggaccaa | ggaaactttc | 300 |
| ccctgatcat | caagaatctt | aagatagaag | actcagatac | ttacatctgt | gaagtggagg | 360 |
| accagaagga | ggaggtgcaa | ttgctagtgt | tcggattgac | tgccaactct | gacacccacc | 420 |
| tgcttcaggg | gcagagcctg | accctgacct | tggagagccc | ccctggtagt | agccctcag | 480 |
| tgcaatgtag | gagtccaagg | ggtaaaaaca | tacaggggg | gaagaccctc | tccgtgtctc | 540 |
| agctggagct | ccaggatagt | ggcacctgga | catgcactgt | cttgcagaac | agaagaagg | 600 |
| tggagttcaa | aatagacatc | gtggtgctag | cttttccagaa | ggcctccagc | atagtctata | 660 |
| agaaagaggg | ggaacaggtg | gagttctcct | tcccactcgc | ctttacagtt | gaaaagctga | 720 |
| cgggcagtgg | cgagctgtgg | tggcaggcgg | agagggcttc | ctcctccaag | tcttggatca | 780 |
| cctttgacct | gaagaacaag | gaagtgtctg | taaaacgggt | tacccaggac | cctaagctcc | 840 |
| agatgggcaa | gaagctcccg | ctccacctca | ccctgcccca | ggccttgcct | cagtatgctg | 900 |
| gctctggaaa | cctcacctg | gcccttgaag | cgaaaacagg | aaagttgcat | caggaagtga | 960 |
| acctggtggt | gatgagagcc | actcagctcc | agaaaatttt | gacctgtgag | gtgtggggac | 1020 |
| ccacctcccc | taagctgatg | ctgagcttga | aactggagaa | caaggaggca | aaggtctcga | 1080 |
| agcgggagaa | ggcggtgtgg | gtgctgaacc | ctgaggcggg | gatgtggcag | tgtctgctga | 1140 |
| gtgactcggg | acaggtcctg | ctggaatcca | acatcaaggt | tctgcccaga | tctaacggtc | 1200 |
| tccctggccc | cattgggccc | cctggtcctc | gcggtcgcac | tggtgatgct | ggtcctgttg | 1260 |
| gtccccccgg | ccctcctgga | cctcctggtc | ccctggtcc | tcccagcgct | ggtttcgact | 1320 |
| tcagcttcct | gccccagcca | cctcaagaga | aggctcacga | tggtggccgc | tactaccggg | 1380 |
| ctgatgatgc | caatgtggtt | cgtgaccgtg | acctcgaggt | ggacaccacc | ctcaagagcc | 1440 |
| tgagccagca | gatcgagaac | atccggagcc | cagagggaag | ccgcaagaac | cccgcccgca | 1500 |
| cctgccgtga | cctcaagatg | tgccactctg | actggaagag | tggagagtac | tggattgacc | 1560 |
| ccaaccaagg | ctgcaacctg | gatgccatca | agtcttctg | caacatggag | actggtgaga | 1620 |
| cctgcgtgta | ccccactcag | cccagtgtgg | cccagaagaa | ctggtacatc | agcaagaacc | 1680 |
| ccaaggacaa | gaggcatgtc | tggttcggcg | agagcatgac | cgatggattc | cagttcgagt | 1740 |
| atggcggcca | gggctccgac | cctgccgatg | tggccatcca | gctgaccttc | ctgcgcctga | 1800 |
| tgtccaccga | ggcctcccag | aacatcacct | accactgcaa | gaacagcgtg | gcctacatgg | 1860 |
| accagcagac | tggcaacctc | aagaaggccc | tgctcctcaa | gggctccaac | gagatcgaga | 1920 |
| tccgcgccga | gggcaacagc | cgcttcacct | acagcgtcac | tgtcgatggc | tgcacgagtc | 1980 |
| acaccggagc | ctggggcaag | acagtgattg | aatacaaaac | caccaagtcc | tcccgcctgc | 2040 |

```
ccatcatcga tgtggccccc ttggacgttg gtgccccaga ccaggaattc ggcttcgacg    2100
ttggccctgt ctgcttcctg taaactccct ccatctaga                           2139
```

<210> SEQ ID NO 14
<211> LENGTH: 699
<212> TYPE: PRT
<213> ORGANISM: Homo sapiens

<400> SEQUENCE: 14

```
Met Asn Arg Gly Val Pro Phe Arg His Leu Leu Leu Val Leu Gln Leu
  1               5                  10                  15

Ala Leu Leu Pro Ala Ala Thr Gln Gly Lys Lys Val Val Leu Gly Lys
             20                  25                  30

Lys Gly Asp Thr Val Glu Leu Thr Cys Thr Ala Ser Gln Lys Lys Ser
         35                  40                  45

Ile Gln Phe His Trp Lys Asn Ser Asn Gln Ile Lys Ile Leu Gly Asn
     50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350
```

Lys Arg Glu Lys Ala Val Trp Val Leu Asn Pro Glu Ala Gly Met Trp
                355                 360                 365

Gln Cys Leu Leu Ser Asp Ser Gly Gln Val Leu Leu Glu Ser Asn Ile
        370                 375                 380

Lys Val Leu Pro Arg Ser Asn Gly Leu Pro Gly Pro Ile Gly Pro Pro
385                 390                 395                 400

Gly Pro Arg Gly Arg Thr Gly Asp Ala Gly Pro Val Gly Pro Pro Gly
                405                 410                 415

Pro Pro Gly Pro Pro Gly Pro Pro Gly Pro Pro Ser Ala Gly Phe Asp
            420                 425                 430

Phe Ser Phe Leu Pro Gln Pro Gln Glu Lys Ala His Asp Gly Gly
        435                 440                 445

Arg Tyr Tyr Arg Ala Asp Asp Ala Asn Val Val Arg Asp Arg Asp Leu
    450                 455                 460

Glu Val Asp Thr Thr Leu Lys Ser Leu Ser Gln Gln Ile Glu Asn Ile
465                 470                 475                 480

Arg Ser Pro Glu Gly Ser Arg Lys Asn Pro Ala Arg Thr Cys Arg Asp
                485                 490                 495

Leu Lys Met Cys His Ser Asp Trp Lys Ser Gly Glu Tyr Trp Ile Asp
            500                 505                 510

Pro Asn Gln Gly Cys Asn Leu Asp Ala Ile Lys Val Phe Cys Asn Met
        515                 520                 525

Glu Thr Gly Glu Thr Cys Val Tyr Pro Thr Gln Pro Ser Val Ala Gln
530                 535                 540

Lys Asn Trp Tyr Ile Ser Lys Asn Pro Lys Asp Lys Arg His Val Trp
545                 550                 555                 560

Phe Gly Glu Ser Met Thr Asp Gly Phe Gln Phe Glu Tyr Gly Gly Gln
                565                 570                 575

Gly Ser Asp Pro Ala Asp Val Ala Ile Gln Leu Thr Phe Leu Arg Leu
            580                 585                 590

Met Ser Thr Glu Ala Ser Gln Asn Ile Thr Tyr His Cys Lys Asn Ser
        595                 600                 605

Val Ala Tyr Met Asp Gln Gln Thr Gly Asn Leu Lys Lys Ala Leu Leu
    610                 615                 620

Leu Lys Gly Ser Asn Glu Ile Glu Ile Arg Ala Glu Gly Asn Ser Arg
625                 630                 635                 640

Phe Thr Tyr Ser Val Thr Val Asp Gly Cys Thr Ser His Thr Gly Ala
                645                 650                 655

Trp Gly Lys Thr Val Ile Glu Tyr Lys Thr Thr Lys Ser Ser Arg Leu
            660                 665                 670

Pro Ile Ile Asp Val Ala Pro Leu Asp Val Gly Ala Pro Asp Gln Glu
        675                 680                 685

Phe Gly Phe Asp Val Gly Pro Val Cys Phe Leu
    690                 695

<210> SEQ ID NO 15
<211> LENGTH: 1947
<212> TYPE: DNA
<213> ORGANISM: Homo sapiens
<220> FEATURE:
<221> NAME/KEY: CDS
<222> LOCATION: (24)...(1931)

<400> SEQUENCE: 15
aagcttccct cggcaaggcc acaatgaacc ggggagtccc ttttaggcac ttgcttctgg      60

```
tgctgcaact ggcgctcctc ccagcagcca ctcagggaaa gaaagtggtg ctgggcaaaa      120
aaggggatac agtggaactg acctgtacag cttcccagaa gaagagcata caattccact      180
ggaaaaactc caaccagata aagattctgg gaaatcaggg ctccttctta actaaaggtc      240
catccaagct gaatgatcgc gctgactcaa gaagaagcct tgggaccaa ggaaactttc       300
ccctgatcat caagaatctt aagatagaag actcagatac ttacatctgt gaagtggagg      360
accagaagga ggaggtgcaa ttgctagtgt tcggattgac tgccaactct gacacccacc      420
tgcttcaggg gcagagcctg accctgacct ggagagcccc cctggtagt agcccctcag       480
tgcaatgtag gagtccaagg ggtaaaaaca tacagggggg gaagaccctc tccgtgtctc      540
agctggagct ccaggatagt ggcacctgga catgcactgt cttgcagaac cagaagaagg      600
tggagttcaa aatagacatc gtggtgctag ctttccagaa ggcctccagc atagtctata      660
agaaagaggg ggaacaggtg gagttctcct tcccactcgc ctttacagtt gaaaagctga      720
cgggcagtgg cgagctgtgg tggcaggcgg agagggcttc ctcctccaag tcttggatca      780
cctttgacct gaagaacaag gaagtgtctg taaaacgggt tacccaggac cctaagctcc      840
agatgggcaa gaagctcccg ctccacctca ccctgccccca ggccttgcct cagtatgctg      900
gctctggaaa cctcacccctg gcccttgaag cgaaaacagg aaagttgcat caggaagtga      960
acctggtggt gatgagagcc actcagctcc agaaaaattt gacctgtgag gtgtggggac      1020
ccacctcccc taagctgatg ctgagcttga aactggagaa caaggaggca aaggtctcga      1080
agcgggagaa ggcggtgtgg gtgctgaacc tgaggcggg gatgtggcag tgtctgctga      1140
gtgactcggg acaggtcctg ctggaatcca acatcaaggt tctgcccaga tctgatgcca      1200
atgtggttcg tgaccgtgac ctcgaggtgg acaccaccct caagagcctg agccagcaga      1260
tcgagaacat ccggagccca gagggaagcc gcaagaaccc cgcccgcacc tgccgtgacc      1320
tcaagatgtg ccactctgac tggaagagtg gagagtactg gattgacccc aaccaaggct      1380
gcaacctgga tgccatcaaa gtcttctgca acatggagac tggtgagacc tgcgtgtacc      1440
ccactcagcc cagtgtggcc cagaagaact ggtacatcag caagaacccc aaggacaaga      1500
ggcatgtctg gttcggcgag agcatgaccg atggattcca gttcgagtat ggcggccagg      1560
gctccgaccc tgccgatgtg gccatccagc tgaccttcct gcgcctgatg tccaccgagg      1620
cctcccagaa catcacctac cactgcaaga acagcgtggc ctacatggac agcagactg      1680
gcaacctcaa gaaggccctg ctcctcaagg gctccaacga gatcgagatc cgcgccgagg      1740
gcaacagccg cttcaccttac agcgtcactg tcgatggctg cacgagtcac accggagcct      1800
ggggcaagac agtgattgaa tacaaaacca ccaagtcctc ccgcctgccc atcatcgatg      1860
tggccccctt ggacgttggt gccccagacc aggaattcgg cttcgacgtt ggccctgtct      1920
gcttcctgta aactccctcc atctaga                                         1947
```

<210> SEQ ID NO 16
<211> LENGTH: 635
<212> TYPE: PRT
<213> ORGANISM: Homo sapiens

<400> SEQUENCE: 16

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser

```
                35              40              45
Ile Gln Phe His Trp Lys Asn Ser Asn Gln Ile Lys Ile Leu Gly Asn
 50                      55                      60

Gln Gly Ser Phe Leu Thr Lys Gly Pro Ser Lys Leu Asn Asp Arg Ala
 65                      70                      75              80

Asp Ser Arg Arg Ser Leu Trp Asp Gln Gly Asn Phe Pro Leu Ile Ile
                 85                      90                      95

Lys Asn Leu Lys Ile Glu Asp Ser Asp Thr Tyr Ile Cys Glu Val Glu
                100                     105                     110

Asp Gln Lys Glu Glu Val Gln Leu Leu Val Phe Gly Leu Thr Ala Asn
                115                     120                     125

Ser Asp Thr His Leu Leu Gln Gly Gln Ser Leu Thr Leu Thr Leu Glu
                130                     135                     140

Ser Pro Pro Gly Ser Ser Pro Ser Val Gln Cys Arg Ser Pro Arg Gly
145                     150                     155                     160

Lys Asn Ile Gln Gly Gly Lys Thr Leu Ser Val Ser Gln Leu Glu Leu
                165                     170                     175

Gln Asp Ser Gly Thr Trp Thr Cys Thr Val Leu Gln Asn Gln Lys Lys
                180                     185                     190

Val Glu Phe Lys Ile Asp Ile Val Val Leu Ala Phe Gln Lys Ala Ser
                195                     200                     205

Ser Ile Val Tyr Lys Lys Glu Gly Glu Gln Val Glu Phe Ser Phe Pro
        210                     215                     220

Leu Ala Phe Thr Val Glu Lys Leu Thr Gly Ser Gly Glu Leu Trp Trp
225                     230                     235                     240

Gln Ala Glu Arg Ala Ser Ser Ser Lys Ser Trp Ile Thr Phe Asp Leu
                245                     250                     255

Lys Asn Lys Glu Val Ser Val Lys Arg Val Thr Gln Asp Pro Lys Leu
                260                     265                     270

Gln Met Gly Lys Lys Leu Pro Leu His Leu Thr Leu Pro Gln Ala Leu
                275                     280                     285

Pro Gln Tyr Ala Gly Ser Gly Asn Leu Thr Leu Ala Leu Glu Ala Lys
        290                     295                     300

Thr Gly Lys Leu His Gln Glu Val Asn Leu Val Val Met Arg Ala Thr
305                     310                     315                     320

Gln Leu Gln Lys Asn Leu Thr Cys Glu Val Trp Gly Pro Thr Ser Pro
                325                     330                     335

Lys Leu Met Leu Ser Leu Lys Leu Glu Asn Lys Glu Ala Lys Val Ser
                340                     345                     350

Lys Arg Glu Lys Ala Val Trp Val Leu Asn Pro Glu Ala Gly Met Trp
                355                     360                     365

Gln Cys Leu Leu Ser Asp Ser Gly Gln Val Leu Leu Glu Ser Asn Ile
        370                     375                     380

Lys Val Leu Pro Arg Ser Asp Ala Asn Val Val Arg Asp Arg Asp Leu
385                     390                     395                     400

Glu Val Asp Thr Thr Leu Lys Ser Leu Ser Gln Gln Ile Glu Asn Ile
                405                     410                     415

Arg Ser Pro Glu Gly Ser Arg Lys Asn Pro Ala Arg Thr Cys Arg Asp
                420                     425                     430

Leu Lys Met Cys His Ser Asp Trp Lys Ser Gly Glu Tyr Trp Ile Asp
                435                     440                     445

Pro Asn Gln Gly Cys Asn Leu Asp Ala Ile Lys Val Phe Cys Asn Met
        450                     455                     460
```

```
Glu Thr Gly Glu Thr Cys Val Tyr Pro Thr Gln Pro Ser Val Ala Gln
465                 470                 475                 480

Lys Asn Trp Tyr Ile Ser Lys Asn Pro Lys Asp Lys Arg His Val Trp
                485                 490                 495

Phe Gly Glu Ser Met Thr Asp Gly Phe Gln Phe Glu Tyr Gly Gly Gln
            500                 505                 510

Gly Ser Asp Pro Ala Asp Val Ala Ile Gln Leu Thr Phe Leu Arg Leu
            515                 520                 525

Met Ser Thr Glu Ala Ser Gln Asn Ile Thr Tyr His Cys Lys Asn Ser
        530                 535                 540

Val Ala Tyr Met Asp Gln Gln Thr Gly Asn Leu Lys Lys Ala Leu Leu
545                 550                 555                 560

Leu Lys Gly Ser Asn Glu Ile Glu Ile Arg Ala Glu Gly Asn Ser Arg
                565                 570                 575

Phe Thr Tyr Ser Val Thr Val Asp Gly Cys Thr Ser His Thr Gly Ala
            580                 585                 590

Trp Gly Lys Thr Val Ile Glu Tyr Lys Thr Thr Lys Ser Ser Arg Leu
            595                 600                 605

Pro Ile Ile Asp Val Ala Pro Leu Asp Val Gly Ala Pro Asp Gln Glu
        610                 615                 620

Phe Gly Phe Asp Val Gly Pro Val Cys Phe Leu
625             630                 635
```